(12) United States Patent
Van Wiemeersch et al.

(10) Patent No.: US 11,975,651 B2
(45) Date of Patent: May 7, 2024

(54) ENHANCED VEHICLE OPERATION

(71) Applicant: Ford Global Technologies, LLC, Dearborn, MI (US)

(72) Inventors: John Robert Van Wiemeersch, Novi, MI (US); Erick Michael Lavoie, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 933 days.

(21) Appl. No.: 16/996,311

(22) Filed: Aug. 18, 2020

(65) Prior Publication Data
US 2022/0054673 A1 Feb. 24, 2022

(51) Int. Cl.
| | |
|---|---|
| A61L 2/04 | (2006.01) |
| A61L 2/10 | (2006.01) |
| A61L 2/24 | (2006.01) |
| B60H 1/00 | (2006.01) |
| B60J 1/20 | (2006.01) |
| B60Q 3/68 | (2017.01) |
| B60S 1/02 | (2006.01) |
| B60S 1/64 | (2006.01) |
| B60R 11/00 | (2006.01) |
| B60R 11/02 | (2006.01) |

(52) U.S. Cl.
CPC ............ *B60Q 3/68* (2017.02); *A61L 2/10* (2013.01); *A61L 2/24* (2013.01); *B60H 1/00042* (2013.01); *B60J 1/20* (2013.01); *B60S 1/02* (2013.01); *B60S 1/64* (2013.01); *A61L 2202/11* (2013.01); *A61L 2202/14* (2013.01); *A61L 2202/25* (2013.01); *B60R 2011/0026* (2013.01); *B60R 11/0235* (2013.01)

(58) Field of Classification Search
CPC ...................................... A61L 2/10; A61L 2/04
See application file for complete search history.

(56) References Cited

U.S. PATENT DOCUMENTS

| 11,584,196 | B2 * | 2/2023 | Kyle | B60H 3/0658 |
| 2019/0076558 | A1 * | 3/2019 | Zhang-Miske | B60Q 3/00 |
| 2021/0339712 | A1 * | 11/2021 | Gutowski | B60H 3/0085 |

OTHER PUBLICATIONS

"Dry Heat Ovens Can Effectively Disinfect N95 Masks", SBU News, Jun. 15, 2020, https://news.stonybrook.edu/sb_medicine/dry-heat-ovens-can-effectively-disinfect-n95-masks/.
"Group looks into resterilizing N95 masks in commercial ovens", The Associated Press, Apr. 3, 2020, https://news.stonybrook.edu/sb_medicine/dry-heat-ovens-can-effectively-disinfect-n95-masks/.
"Industrial Oven-Maker Testing Dry Heat Sterilization on PPE and N95 Masks", Industrial News, Apr. 6, 2020, Copyright © 2020. All Rights Reserved BNP Media.

(Continued)

*Primary Examiner* — Donald R Spamer
(74) *Attorney, Agent, or Firm* — Frank Lollo; Bejin Bieneman PLC

(57) ABSTRACT

A computer includes a processor and a memory, the memory storing instructions executable by the processor to, heat a passenger cabin of a vehicle, actuate a thermal sensor to collect temperature data in the passenger cabin, identify a surface in the passenger cabin that has a temperature below a temperature threshold, and actuate one or more components to sanitize the identified surface.

20 Claims, 8 Drawing Sheets

(56) References Cited

OTHER PUBLICATIONS

"Michigan soldiers set to use giant oven in the war on COVID-19", Jun. 15, 2020, Detroit Free Press, https://www.msn.com/en-us/news/us/michigan-soldiers-set-to-use-giant-oven-in-the-war-on-covid-19/ar-BB12zxOI.

Chan et al., "The Effects of Temperature and Relative Humidity on the Viability of the SARS Coronavirus", Research Article:Open Access, Jun. 15, 2020, vol. 2011, Article ID 734690, https://www.hindawi.com/journals/av/2011/734690/.

"First data on stability and resistance of SARS coronavirus compiled by members of WHO laboratory network", World Health Organization, Jun. 15, 2020, https://www.who.int/csr/sars/survival_2003_05_04/en/.

\* cited by examiner

ENHANCED VEHICLE OPERATION

BACKGROUND

Vehicles can be equipped with computers, networks, sensors and controllers to acquire data regarding the vehicle's environment and to operate the vehicle based on the data. For example, the computer can actuate one or more components to control a temperature of a passenger cabin.

DETAILED DESCRIPTION

Introduction

Figure 1:
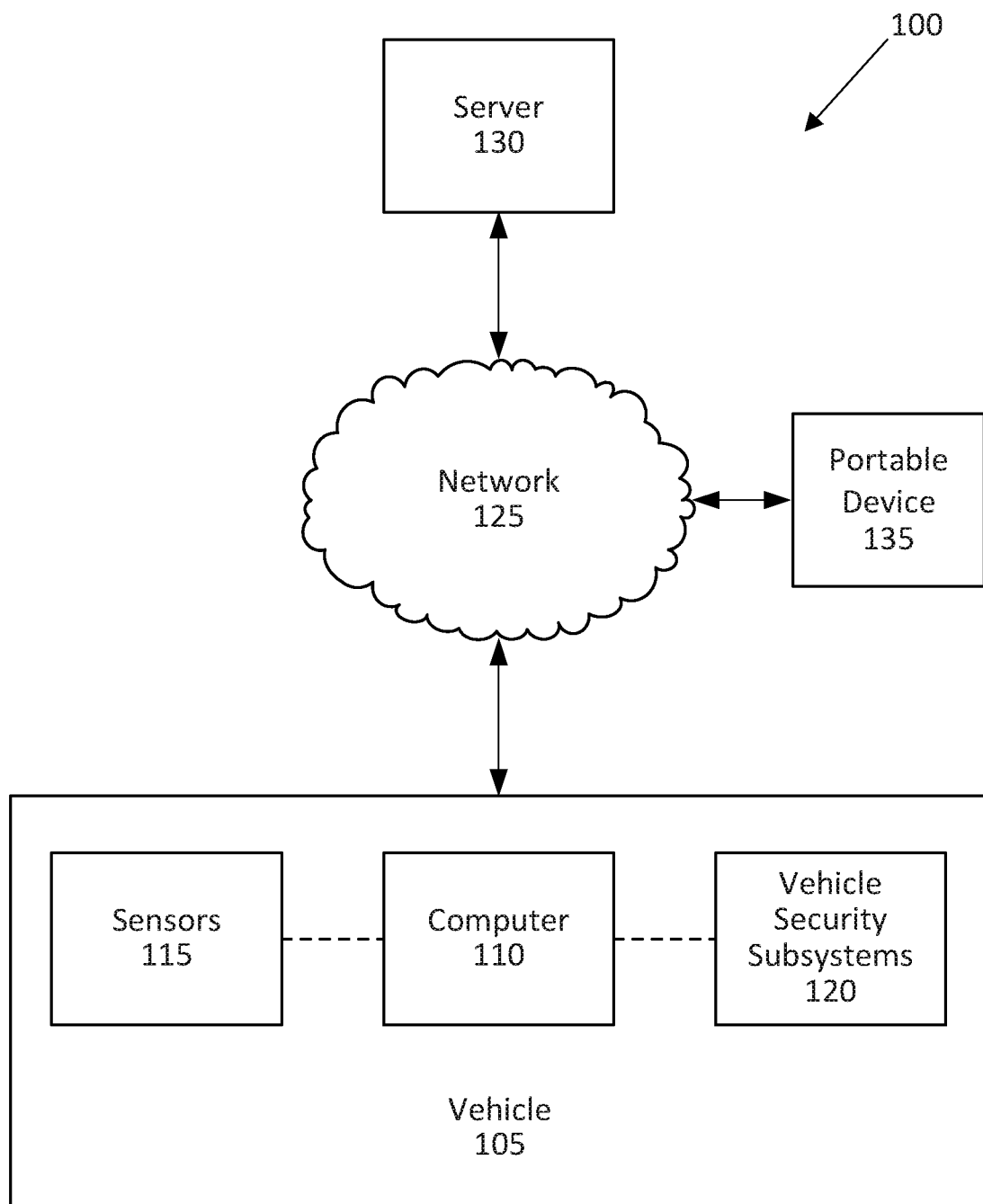
FIG. 1 is a diagram of an example system for controlling cabin temperature in a vehicle.

Reducing pathogens, such as bacteria and viruses, in a vehicle can reduce transmission of the pathogens to users of the vehicle. Heat can reduce pathogens, and thus increasing a temperature of air in the vehicle, e.g., in a vehicle cabin, cargo compartment, etc., can reduce pathogens in the vehicle. For example, increasing ambient temperature in a closed space such as a vehicle passenger cabin above a specified threshold, e.g., 133 degrees Fahrenheit (approximately 56 degrees Celsius), can eliminate various pathogens, including strains of bacteria and viruses. Maintaining ambient temperature at or above this threshold for a specified amount of time, e.g., 15 minutes, can reduce pathogens in the vehicle such that users who contact surfaces in the vehicle would not likely receive, i.e., inhale, absorb, or carry on their skin, clothing, etc., live pathogens from the surfaces, reducing transmission of the pathogens.

Vehicles include a plurality of components that can provide heat to a passenger cabin. For example, a climate control component can heat air with excess heat from a propulsion engine and/or a heater. In another example, a heating mechanism such as an electric wire or metallic particles embedded in a window can increase a temperature of glass, e.g., surrounding the wire or the areas with embedded metalized particles, thus reducing pathogens on a surface of the glass. A computer in the vehicle can control one or more components to heat the passenger cabin to reduce the pathogens. Different components can heat the passenger cabin in different ways and/or at different rates. For example, the electric wire or metallic particles embedded in the window can heat the glass of the window, while a fuel-operated heater in the passenger cabin can heat air in the passenger cabin and gradually increase the temperature of all cabin surfaces. It is a challenge for the computer to determine which components to actuate to heat each portion of the passenger cabin to reduce the pathogens. This presents a technical challenge for the computer. For example, because different portions of the vehicle may heat at different rates, determining the components to heat the entire vehicle to account for the different heating rates can be difficult without obtaining and considering additional data about, e.g., the temperature of specific surfaces of the vehicle, ambient environment conditions that can slow heating of the vehicle, etc.

Planning vehicle component actuation to heat a vehicle compartment based on user input, ambient environmental data, and temperature data of specific parts of the vehicle allows the computer to heat the entire passenger cabin to reduce the pathogens. That is, the computer can use data from one or more, and typically a plurality of, sources of input to determine one or more components to actuate to heat the vehicle. Selective actuation of components for heating allows for a more energy efficient heating of the vehicle than actuating the components without the data from the plurality of sources. Using heat sources external to the vehicle, such as insolation from the sun and ambient air, can improve heating of the vehicle when used in conjunction with components in the vehicle by reducing the output from the components. Thus, the presently disclosed system can reduce the pathogens in the vehicle prior to use by a user.

System Overview

FIG. 1 illustrates an example system 100 for operating a vehicle 105. A computer 110 in the vehicle 105 is programmed to receive collected data from one or more sensors 115. For example, vehicle data may include a location and orientation of the vehicle 105, data about an environment around a vehicle 105, data about an object outside the vehicle 105 such as another vehicle 105, etc. A vehicle location is typically provided in a conventional form, e.g., geo-coordinates such as latitude and longitude coordinates obtained via a navigation system that uses the Global Positioning system (GPS). Further examples of data can include measurements of vehicle systems and components, e.g., a vehicle velocity, a vehicle trajectory, etc.

The computer 110 is generally programmed for communications on a vehicle network, e.g., including a conventional vehicle communications bus such as a CAN bus, LIN bus, etc., and or other wired and/or wireless technologies, e.g., Ethernet, Bluetooth®, Ultra Wideband (UWB), WIFI, LiFi, ultrasonic communication, etc. Via the network, bus, and/or other wired or wireless mechanisms (e.g., a wired or wireless local area network in the vehicle 105), the computer 110 may transmit messages to various devices in a vehicle 105 and/or receive messages from the various devices, e.g., controllers, actuators, sensors 115, etc. Alternatively, or additionally, in cases where the computer 110 actually comprises multiple devices, the vehicle network may be used for communications between devices represented as the computer 110 in this disclosure. The computer 110 can be a generic computer 110 with a processor and memory as described above and/or may include a dedicated electronic circuit including an ASIC (Application Specific Integrated Circuit) that is manufactured for a particular operation, e.g., an ASIC for processing sensor data and/or communicating the sensor data. In another example, the computer 110 may include an FPGA (Field-Programmable Gate Array) which is an integrated circuit manufactured to be configurable by a user. Typically, a hardware description language such as VHDL (Very High Speed Integrated Circuit Hardware Description Language) is used in electronic design automation to describe digital and mixed-signal systems 100 such as FPGA and ASIC. For example, an ASIC is manufactured based on VHDL programming provided pre-manufacturing, whereas logical components inside an FPGA may be configured based on VHDL programming, e.g. stored in a memory electrically connected to the FPGA circuit. In some examples, a combination of processor(s), ASIC(s), and/or FPGA circuits may be included in computer 110.

In addition, the computer 110 may be programmed for communicating with the network 125, which, as described below, may include various wired and/or wireless networking technologies, e.g., cellular, Bluetooth®, Bluetooth® Low Energy (BLE), wired and/or wireless packet networks such as Ultra Wideband (UWB), WIFI, LiFi, ultrasonic communication, etc.

The memory can be of any type, e.g., flash, hard disk drives, solid state drives, servers, or any volatile or non-volatile media. The memory can store the collected data sent from the sensors 115. The memory can be a separate device from the computer 110, and the computer 110 can retrieve data stored by the memory via a network in the vehicle 105, e.g., over a CAN bus, a wireless network, etc. Alternatively, or additionally, the memory can be part of the computer 110, e.g., as a memory of the computer 110.

Sensors 115 can include a variety of devices that collect data. For example, various controllers in a vehicle 105 may operate as sensors 115 to provide data via the vehicle network or bus, e.g., data relating to vehicle speed, acceleration, location, orientation, subsystem and/or component status, etc. Further, other sensors 115 could include cameras, motion detectors, etc., i.e., sensors 115 to provide data for evaluating a position of a component, evaluating a slope of a roadway, etc. The sensors 115 could, without limitation, also include short range radar, long range radar, LIDAR, and/or ultrasonic transducers.

Collected data can include a variety of data collected in a vehicle 105. Examples of collected data are provided above, and moreover, data are generally collected using one or more sensors 115, and may additionally include data calculated therefrom in the computer 110, and/or at the server. In general, collected data may include any data that may be gathered by the sensors 115 and/or computed from such data.

The vehicle 105 can include one or more sensors 115 that detect objects external to the vehicle 105. In one example, the sensors 115 can include a proximity motion sensor 115. A "proximity motion" sensor 115 is a sensor 115 that detects movement within a predetermined distance from the sensor 115. That is, the proximity motion sensor 115 can use a Fresnel lens with a pair of slots in a field of view of the lens that detect electromagnetic (EM) waves, e.g., infrared (IR) waves. When the proximity motion sensor 115 detects IR waves through one of the pair of slots and not the other pair of slots (e.g., from a moving object), the proximity motion sensor 115 detects a difference in IR waves collected by each slot. When the difference in IR exceeds a threshold, the computer 110 can determine that an object moved into the field of view of the sensor 115. The threshold can be a predetermined value based on empirical testing of test objects moving at specified speeds past the proximity motion sensor 115. The proximity motion sensor 115 can be programmed with a plurality of thresholds to detect objects with different sensitivities. That is, each threshold can detect motion of objects above a respective specified speed. In another example, the sensors 115 can include a camera, i.e., a sensor 115 that collects image data.

A vehicle 105 can operate in one of a fully autonomous mode, a semiautonomous mode, or a non-autonomous mode. A fully autonomous mode is defined as one in which each of vehicle 105 propulsion (typically via a powertrain including an electric motor and/or internal combustion engine), braking, and steering are controlled by the computer 110 of the vehicle 105. A semi-autonomous mode is one in which at least one of vehicle 105 propulsion (typically via a powertrain including an electric motor and/or internal combustion engine), braking, and steering are controlled at least partly by the computer 110 as opposed to a human operator. In a non-autonomous mode, i.e., a manual mode, the vehicle 105 propulsion, braking, and steering are controlled by the human operator.

The computer 110 can actuate a vehicle security subsystem 120 to prevent mobility of the vehicle 105. A "vehicle security subsystem" 120 is a device and/or programming of the computer 110 that performs an action to prevent access to the passenger cabin 200 and/or prevent mobility of the vehicle 105 and/or detect an object that could interfere with operation of the vehicle 105. The vehicle security subsystem 120 provides security for the user of the vehicle 105 by identifying and/or preventing threats to the vehicle 105 and preventing unauthorized access to a cabin of the vehicle 105 and/or preventing the vehicle 105 from unauthorized moving during the sanitizing operation.

The system 100 can further include a network 125 connected to a server 130. The computer 110 can further be programmed to communicate with one or more remote sites such as the server 130, via the network 125, such remote site possibly including a processor and a memory. The network 125 represents one or more mechanisms by which a vehicle 105 computer 110 may communicate with a remote server 130. Accordingly, the network 125 can be one or more of various wired or wireless communication mechanisms, including any desired combination of wired (e.g., cable and fiber) and/or wireless (e.g., cellular, wireless, satellite, microwave, and radio frequency) communication mechanisms and any desired network 125 topology (or topologies when multiple communication mechanisms are utilized). Exemplary communication networks 125 include wireless communication networks 125 (e.g., using Bluetooth®, Bluetooth® Low Energy (BLE), Ultra Wideband (UWB), IEEE 802.11, LiFi, ultrasonic communication, vehicle-to-vehicle (V2V) such as Dedicated Short Range Communications (DSRC), etc.), local area networks (LAN) and/or wide area networks (WAN), including the Internet, providing data communication services.

The portable device 135 may be any one of a variety of devices, such as computing devices including a processor and a memory, that have communication capabilities to communicate over the network 125. For example, the portable device 135 may be a wearable device, e.g. a watch or a smart watch, a smartphone, a tablet, a personal digital assistant, a watch-phone pairing, a vibrating apparatus, etc. that includes capabilities for wireless communications using IEEE 802.11, Bluetooth®, UWB, NFC, and/or cellular communications protocols. Further, the portable device 135 may use such communications capabilities to communicate directly with a vehicle computer 110, e.g., using Bluetooth®.

Vehicle Heating and Sanitizing

Figure 2:
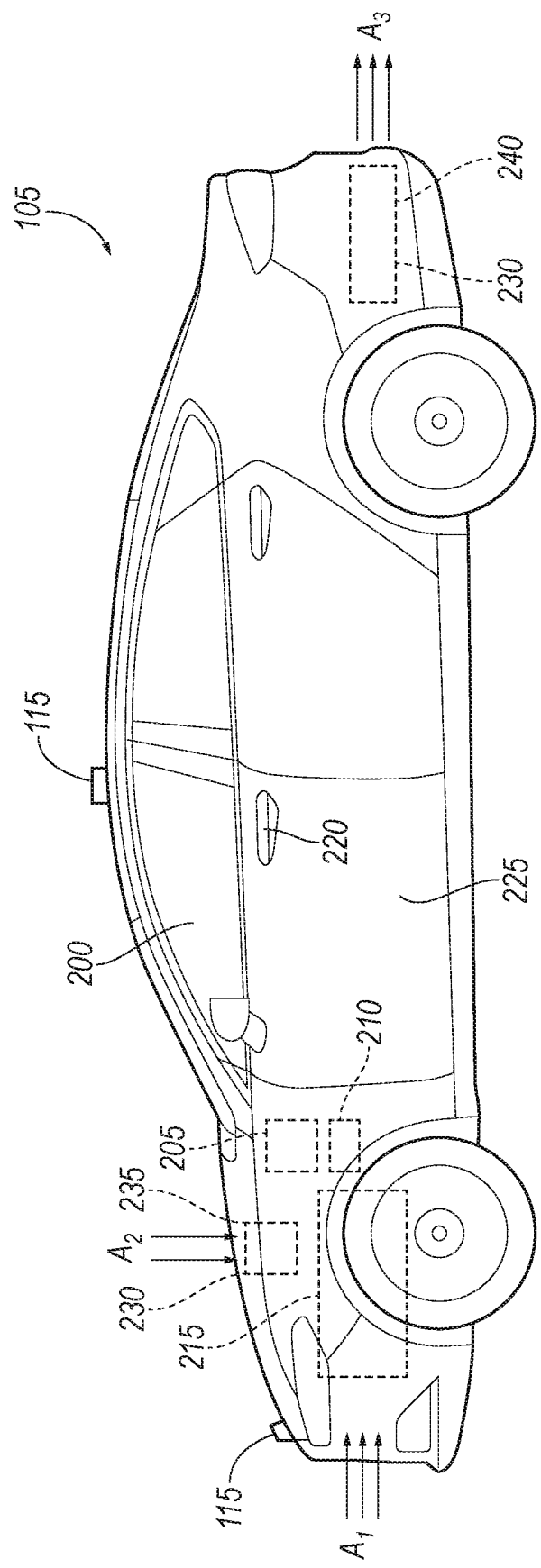
FIG. 2 is a side view of an example vehicle that includes the system of FIG. 1.

FIG. 2 is a side view of an example vehicle 105. The vehicle 105 includes a passenger cabin 200. The passenger cabin 200 is an interior portion of the vehicle 105 that can be occupied by users of the vehicle 105. Air and surfaces in the passenger cabin 200 can be heated or cooled to a specific temperature, e.g., set according to user input to a vehicle climate control system. The computer 110 can communicate via a vehicle network with one or more components, controllers, and/or devices, as described below, to increase a temperature of air in the passenger cabin 200.

The computer 110 can sanitize the vehicle 105 according to a sanitizing operation. In this context, to "sanitize" the vehicle 105 means to reduce pathogens to below a specified level, e.g., by increasing a temperature of air in the passenger cabin 200 of the vehicle 105 above a temperature threshold and maintaining the temperature of the air above the temperature threshold for an elapsed time exceeding a time threshold. The temperature threshold and time threshold are typically selected to cause reduction or even elimination of pathogens. A "pathogen" is an organism that can cause a disease, e.g., a virus, a bacterium, a fungus, a parasite, etc. A "sanitizing operation" means actuating components, controllers, and/or devices to sanitize the vehicle 105. The temperature threshold can be a temperature at which the heat reduces an amount of a pathogen (e.g., bacteria, viruses, etc.). The time threshold can be a specified period of time for the pathogen to be reduced to a specified amount at a temperature at or above the temperature threshold. Such times and temperatures are known for a wide variety of pathogens. To provide just one example, if the pathogen is a virus, according to data from the World Health Organization (WHO) about Severe Acute Respiratory Syndrome (SARS) coronavirus survivability, the temperature threshold can be 133 degrees Fahrenheit (56 degrees Celsius) and the time threshold can be 15 minutes to eliminate 10000 viruses. Thus, in one example, to sanitize the vehicle 105, the computer 110 can heat air in the interior of the vehicle 105 to a temperature above 133 degrees Fahrenheit and maintain the temperature for at least 15 minutes. In another example, the computer 110 can heat air in the interior of the vehicle 105 for a duration empirically determined to also allow target surfaces to achieve the specified temperature. That is, an air temperature can change more rapidly than surface temperatures because the surfaces have greater masses and thermal conductivities than the air in the passenger cabin 200. Sanitizing of at least some surfaces can be assisted by direct sunlight, which can increase heating of the surfaces, and other surfaces may heat more slowly if obscured from sunlight by shade. When the elapsed time exceeds the time threshold, the computer 110 can deactivate the components, controllers, and/or devices described above to allow the passenger cabin to cool.

The computer 110 can increase the temperature of the passenger cabin 200. The vehicle 105 can include one or more heater(s) 205. A heater 205 is a device that increases its temperature to increase the temperature of a working fluid. For example, a heater 205 can include resistive coils that, when electricity flows through the resistive coils, generates heat to heat surrounding air. In another example, a heater 205 can include a burner for a combustible fuel (e.g., gasoline, natural gas, etc.) that, upon combusting, generates heat. Air heated by a heater 205 can be pumped to heat, e.g., the passenger cabin 200. Alternatively, or additionally, a heater 205 can be a device located in the passenger cabin 200, part of a climate control component, as described below, and/or the heater 205 can be a heating element installed in one or more parts of the passenger cabin 200, e.g., a heating element in a seat, a heating element in a steering wheel, etc.

The computer 110 can predict an ambient temperature at a location of the vehicle 105. The "ambient temperature" of a location of the vehicle 105, sometimes referred to as ambient environmental temperature, or ambient temperature of the environment, is the temperature of the air external to the vehicle 105. The computer 110 can determine the ambient air temperature of an environment with, e.g., a temperature sensor 115. Alternatively, or additionally, the computer 110 can receive the ambient temperature from a remote server 130 via the network 125. The computer 110 can predict a time to heat the passenger cabin based on the predicted ambient temperature using, e.g., insolation, the position of the sun, the location of the vehicle 105, etc., input to conventional thermal models. That is, the computer 110 can use the conventional thermal models to predict the increase in temperature of the passenger cabin 200 caused by the ambient temperature and other environmental factors. For example, if the ambient temperature is predicted to decrease, the computer 110 can determine candidate initiation times that would allow the heater 205 to heat the passenger cabin 200 for a longer period of time than if the ambient temperature is predicted to remain static or increase. The computer 110 can output the ambient temperature, insolation data (e.g., from an insolation model), and the predicted time to heat the passenger cabin 200 to the user.

The vehicle 105 can include a transmission 210. The transmission 210 is arranged to transfer output from a propulsion subsystem 215 to wheels of the vehicle 105. For example, the transmission 210 can include one or more gears that transfer output of the propulsion subsystem 215 to the wheels. The transmission 210 can transfer the output in one of a plurality of operation modes. An "operation mode" is a configuration of the transmission 210 that provides a specific output from the propulsion subsystem 215 to the wheels. For example, in a "park" operation mode, the transmission 210 provides no output from the propulsion subsystem 215 to the wheels which prevents movement of the wheels. In another example, in a "neutral" operation mode, the transmission 210 provides no output from the propulsion subsystem 215 to the wheels but allows movement of the wheels. In another example, in a "drive" operation mode, the transmission 210 transfers output from the propulsion subsystem 215 to the wheels. The computer 110 can restrict the transmission 210 to the park mode to prevent mobility of the vehicle 105. In this context, "mobility" is the ability for the vehicle 105 to move from a current position. That is, when the transmission 210 is restricted to the park mode, the computer 110 ignores input to move the transmission 210 to a different transmission mode. Restricting the transmission 210 to the park mode prevents mobility of the vehicle 105 during a sanitizing operation. If the vehicle 105 is operating in a fully autonomous mode without users in the passenger cabin 200, the computer 110 can allow operation of the transmission 210 to, e.g., perform the sanitizing operation while the vehicle 105 is in motion.

The vehicle 105 can include the propulsion subsystem 215. The propulsion subsystem 215 propels the vehicle 105. That is, the propulsion subsystem 215 converts electrical energy from an electric motor and/or chemical energy from a combustible fuel to rotation of wheels via the transmission 210. The propulsion subsystem 215 can be one or more of, e.g., an internal combustion engine, an electric motor, etc. The propulsion subsystem 215 can include engine coolant to cool the propulsion subsystem 215. When the engine coolant cools the propulsion subsystem 215, the temperature of the engine coolant increases. That is, the engine coolant can receive heat from the propulsion subsystem 215 via, e.g., a heat exchanger. Air can enter the propulsion subsystem 215 (or a housing or compartment thereof) through an opening in a vehicle exterior surface, e.g., a front grill of the vehicle 105; air flow to the propulsion subsystem 215 in such example is shown in FIG. 2 as arrows labeled $A_1$. The computer 110 can use both the heater 205 and the propulsion subsystem 215 to perform the sanitizing operation faster than using either the heater 205 or the propulsion system 215 alone.

The vehicle 105 can include a door latch 220 for a vehicle door 225. The door latch 220 secures the door 225 to the rest of the vehicle body, preventing entry into and/or exit from the vehicle 105. The door latch 220 can be disposed on an exterior portion of the door 225 and can include an exterior door handle. The user can pull on the exterior door handle to engage the door latch 220 to unlatch the door 225. Alternatively, or additionally, the door latch 220 can be disposed in an interior portion of the door 225 and include an interior door handle. The user can pull on the interior door handle to engage the latch 220 to unlatch the door 225.

The door latch 220 can include an internal lock. The internal lock can prevent unlatching of the door 225 to secure the door 225 to the vehicle body, preventing opening of the door 225 from the passenger cabin 200. That is, the internal lock can include a pawl (not shown) that engages a striker (not shown) to secure the door 225 to the vehicle body. The internal lock can be actuated to a "double-lock" mode. In the double-lock mode, the pawl engages the striker to prevent opening of the door 225 from both the external door handle and the internal door handle. That is, in the double-lock mode, the door 225 cannot be opened by the external door handle or the internal door handle. The double-lock mode prevents opening of the door 225, preventing the heated air of the passenger cabin 200 from exiting. In another example, the door latch 220 can be a fully electronic door latch 220 (i.e., an "e-Latch"), and the computer 110 can suppress powering of a release motor of the e-Latch during the sanitizing operation to prevent unlatching and opening of the door 225.

The computer 110 can actuate the internal lock or inhibit release of the e-Latch as described above while the temperature of the passenger cabin 200 exceeds the threshold. The computer 110 can release the internal lock or allow release of the e-Latch when the temperature of the passenger cabin 200 falls below the second threshold. Alternatively, or additionally, the computer 110 can release the internal lock or allow release of the e-Latch upon receiving a request from an user external to the vehicle 105, e.g., via input to a portable device 135 wirelessly provided to the computer 110, e.g., via Bluetooth® or the like. The computer 110 can actuate the internal lock or suppress release of the e-Latch in a double-lock mode, i.e., preventing unlocking or unlatching of the door 225 from both the external door handle or the internal door handle of the door latch 220.

The computer 110 can be programmed to confirm that criteria are met and/or to meet criteria for initiating a sanitization process. For example, the computer 110 can be programmed to enclose the passenger cabin 200 and prevent mobility of the vehicle 105 prior to the identified initiation time. Enclosing the passenger cabin 200 prevents heated air from exiting the passenger cabin 200. Heated air exiting the passenger cabin 200 can decrease the temperature of the passenger cabin 200, preventing sanitization and/or causing the heater 205 to increase output and lengthening the sanitizing operation longer than the sanitizing operation would occur for an enclosed passenger cabin 200. Preventing mobility of the vehicle 105 prevents other users from moving the vehicle 105 and/or disturbing the sanitizing operation. For example, the computer 110 can actuate one or more motors to close the windows of the vehicle 105. In another example, the computer 110 can restrict the transmission 210 to the park mode, as described above. In another example, the computer 110 can determine that the vehicle 105 is in a "safe" location, i.e., a location at which the vehicle 105 is unlikely to be disturbed during the sanitizing operation. In another example, the computer 110 can actuate a power door component to close the doors 225.

The vehicle 105 can include a climate control component 230. The climate control component 230 can include an air blower 235 and an air pump 240. The climate control component 230 can control the temperature of the passenger cabin 200. For example, a user can actuate the climate control component 230 to maintain a specified temperature of the passenger cabin 200, e.g., 72 degrees Fahrenheit. The climate control components 230 typically includes one or more devices to control the temperature of the passenger cabin 200, e.g., the heater 205, a compressor to cool air, the air blower 235 to provide the heated or cooled air to the passenger cabin, a human-machine interface (HMI) to receive user input indicating a specified cabin temperature, an electronic controller that is programmed to actuate the heater 205, the compressor, and the air blower 235, etc. Upon receiving user input indicating a specified cabin temperature, the computer 110 can actuate the heater 205 or the compressor to heat or cool air. The computer 110 can actuate the air blower 235 to provide the heated or cooled air to the passenger cabin 200, increasing or decreasing the temperature of the passenger cabin 200 to the specified cabin temperature. The computer 110 can actuate the heater 205 or the compressor according to a conventional heating and cooling algorithm, e.g., proportional-integral-derivative (PID) control.

The climate control component 230 can use heat from the heated engine coolant to heat the passenger cabin 200. Alternatively, or additionally, the climate control component 230 can use heat from the heater 205 to heat the passenger cabin 200. The air blower 235 moves air from the propulsion 215 and/or the heater 205 to the passenger cabin 200 to heat the passenger cabin 200. The air pump 240 allows air to exit the passenger cabin 200. That is, the air blower 235 is arranged to provide heated air to the passenger cabin 200 and the air pump 240 is arranged to provide air flow into and out from the passenger cabin 200. The air pump 240 can be, e.g., a motorized air extractor that uses a motor to move air out the passenger cabin 200, move air into the passenger cabin 200, close one or more louvers, and/or open one or more louvers to allow movement of the air by air pressure generated by the air blower 235. Air flow to the air blower 235 is shown as arrows in FIG. 2 labeled $A_2$. If the ambient external air temperature exceeds the temperature of the air in the passenger cabin, the computer 110 can actuate the motor of the air pump 240 to introduce air external to the vehicle 105. That is, the computer 110 can introduce air that is hotter than the air of the passenger cabin 200, heating the passenger cabin 200. Alternatively, if the ambient external air temperature is below the temperature of the air in the passenger cabin, the computer 110 can close all external air passages (e.g., windows, doors, louvers, etc.) to minimize exhausting of air in the passenger cabin 200 during the sanitizing operation. That is, closing the external air passages prevents air from exiting the passenger cabin 200 during the sanitizing operation, preventing pathogens in the air from exiting the vehicle and reducing heat loss from the passenger cabin 200. The computer 110 can close the external air passages upon detecting pedestrians within a distance threshold of the vehicle 105, e.g., 2 meters.

The computer 110 can suppress a climate control limiter of the climate control component 230. The "climate control limiter" is programming of an electronic controller of the climate control component 230 that prevents the air blower 235 from operating when an engine coolant temperature exceeds a temperature threshold. That is, the climate control limiter prevents heating operation of the climate control component 230 when heating may not be required (e.g., during hot summer weather) and prevents cooling operation of the climate control component 230 when cooling may not be required (e.g., during cold winter weather). Upon suppressing the climate control limiter, the computer 110 can actuate the air blower 235 of the climate control component 230 to provide air to the heater 205 to heat the passenger cabin 200.

Upon suppressing the climate control limiter, the computer 110 can actuate a motor on the air pump 240 to introduce air external to the vehicle 105 to the passenger cabin. The external air can be warmer than the air in the vehicle 105, and the air pump 240 can introduce the warmer external air to the heater 205 to heat the passenger cabin 200 more quickly than using the air in the vehicle 105. Alternatively, or additionally, the computer 110 can actuate the window when the temperature of air external to the vehicle 105 exceeds the temperature of the passenger cabin 200. Yet alternatively or additionally, the computer 110 can actuate the air pump 240 to remove air from the passenger cabin 200 that is cooler than the external air.

The computer 110 can actuate the climate control limiter when the temperature of the passenger cabin 200 exceeds a second temperature threshold. After sanitizing the vehicle 105, the computer 110 no longer needs to actuate the climate control component 230 to heat the passenger cabin 200, and the computer 110 can actuate the climate control limiter to prevent the air blower 235 from operating. That is, the computer 110 can return the climate control component 230 to a default setting in which the climate control limiter limits operation of the air blower 235.

The computer 110 can actuate the air pump 240 to remove air from the passenger cabin 200 when the temperature of the passenger cabin exceeds the temperature threshold. That is, the computer 110 can remove air from the passenger cabin 200 when the temperature of the passenger cabin 200 exceeds the temperature threshold for a period of time exceeding the time threshold and completing the sanitizing operation. After sanitizing the vehicle 105, the computer 110 can actuate the air pump 240 to purge the heated air from the passenger cabin 200, replacing the heated air with cooler air external to the vehicle 105, reducing the temperature of the passenger cabin 200. The purged air is shown in FIG. 2 with arrows labeled $A_3$. Purging the hot air from the passenger cabin 200 cools the passenger cabin 200 more quickly than allowing the hot air to remain in the passenger cabin 200. Alternatively, or additionally, the computer 110 can actuate the air blower 235 to introduce air external to the vehicle 105 to the passenger cabin 200, cooling the passenger cabin 200.

The computer 110 can transition the climate control component 230 from a recirculation mode in which air in the passenger cabin 200 is reintroduced to the climate control component 230 to an external mode in which the air blower 235 and the air pump 240 to purge the air from the passenger cabin 200 and introduce external air to the passenger cabin 200. The computer 110 can transition the climate control component 230 from the recirculation mode upon determining that the user will use the vehicle 105 before the heated air in the passenger cabin 200 can cool below the second temperature threshold. Additionally, or alternatively, the computer 110 can, at the beginning of the sanitizing operation, transition the climate control component 230 from the recirculation mode if the temperature of the external air exceeds the temperature of the air in the passenger cabin 200. Then, during the sanitizing operation, when the temperature of the air in the passenger cabin 200 exceeds the temperature of the external air, the computer 110 can transition the climate control component 230 to the recirculation mode to keep the heated air in the vehicle 105.

The computer 110 can determine whether the vehicle 105 is in an enclosed space. An "enclosed space" is a space that includes one or more barriers to limit flow of air external to the vehicle. The enclosed space can be, e.g., a garage, a parking structure, etc. The computer 110 can actuate one or more sensors 115 to detect the barriers that limit air flow, e.g., walls, a ceiling, etc. If the computer 110 determines that the vehicle 105 is in an enclosed space, the computer 110 can suppress operation of an internal combustion engine the propulsion subsystem 215 to prevent exhaust from accumulating in the enclosed space.

Vehicle Passenger Cabin

Figure 3:
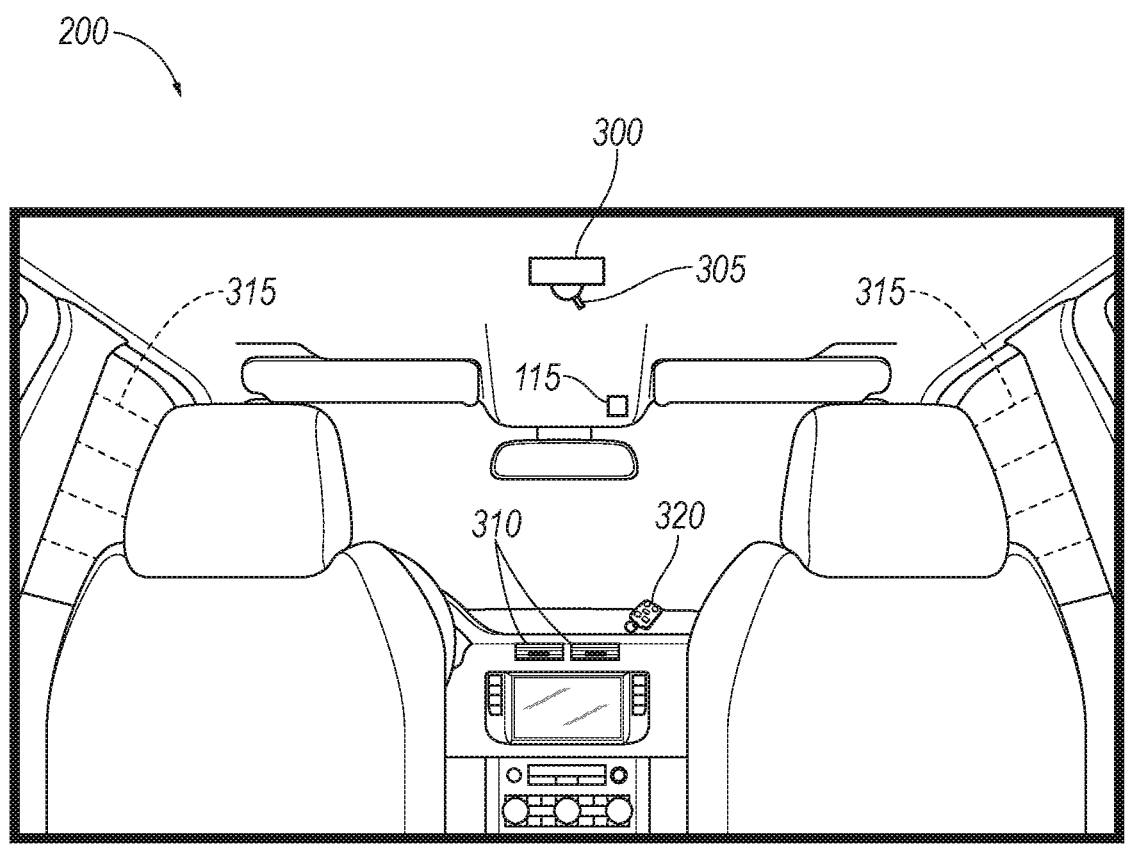
FIG. 3 is a view of a passenger cabin of the vehicle of FIG. 2.

FIG. 3 is a view of the passenger cabin 200 of the vehicle 105. The passenger cabin 200 includes a plurality of components and/or devices that the computer 110 can actuate to heat the passenger cabin 200. The vehicle 105 can include a thermal sensor 115. The thermal sensor 115 collects temperature data from surfaces in the passenger cabin 200. A "surface" is a part of a component or other part of the vehicle 105 exposed to the air of the passenger cabin 200. The user may come into physical contact with one or more of the surfaces, contacting pathogens that may be on the surfaces. The thermal sensors 115 can be disposed in the passenger cabin 200 to collect temperature data on surfaces in the passenger cabin 200. For example, the thermal sensors 115 can be disposed on an interior ceiling of the passenger cabin 200 such that the respective fields of view of the thermal sensors 115 collect data of surfaces in the passenger cabin. Alternatively, or additionally, the thermal sensors 115 can be disposed on, e.g., a pillar, a dashboard, an instrument panel, a window, a windshield, a seat, etc. Pathogens may be located on the surfaces, and the computer 110 can actuate one or more components to sanitize the surfaces. Surfaces can include, e.g., a seat cushion, a window pane, a dashboard, a rearview mirror, etc. The thermal sensor 115 can be, e.g., an infrared sensor 115 that detects infrared (IR) electromagnetic waves emitted by the surfaces, i.e., electromagnetic waves having wavelengths between 700-1000 nanometers (nm). The computer 110 can determine the temperature of the surface based on the collected data about the IR waves using a conventional correlation, e.g., blackbody radiation charts, Kirchoff's law of thermal radiation, etc.

The computer 110 can identify one or more surfaces in the vehicle 105 having a temperature below the temperature threshold. The surface can be in any compartment of the vehicle 105, e.g., the passenger cabin 200, a trunk, a cargo compartment, etc. That is, the surface identified in thermal data can have a temperature below the temperature threshold. For example, the identified surface can be a surface of a seat. In another example, the surface can be a portion of a window. Upon identifying the one or more surfaces, the computer 110 can sanitize the surfaces by increasing the temperature of the surface above the temperature threshold.

When air temperature in the passenger cabin 200 exceeds the temperature threshold, the computer 110 can actuate the thermal sensor 115 to collect temperature data of a plurality of surfaces in the interior of the vehicle 105. As described above, a surface is a part of a component or other part of the vehicle 105 exposed to the air of the passenger cabin. While the temperature of the air may exceed the sanitizing temperature, one or more surfaces may still be below the sanitizing temperature. That is, the thermal properties of the material of the surface may cause the surface to remain below the temperature threshold. For example, a material with a higher thermal conductivity than a thermal conductivity of air requires more energy to exceed the temperature threshold than the air does, and the material may thus remain below the temperature threshold even when the air is above the temperature threshold.

The thermal sensor 115 can be, e.g., an infrared (IR) sensor 115 that detects a temperature of the surface. That is, the IR sensor 115 can collect data about IR waves emitted by the surface, and the computer 110 can, using conventional thermal models such as blackbody radiation algorithms that use the Stefan-Boltzmann temperature law, determine the temperature of the surface based on the IR waves emitted by the surface. That is, IR waves j are generated by a surface at a temperature T according to the Stefan-Boltzmann law:

$$j = \varepsilon \sigma T^4 \quad (1)$$

where $\sigma$ is the Stefan-Boltzmann constant and $\varepsilon$ is an emissivity of the surface. The emissivity $\varepsilon$ can typically be approximated as 0.75-0.85 for typical surfaces in a vehicle 105 and can be determined empirically by measuring the IR waves j emitted from the surface when the surface is at a specified temperature T. Thus, by retrieving a stored value for the emissivity $\vartheta$, the computer 110 can determine a temperature T of a surface based on IR waves j detected by the thermal sensor 115.

The vehicle 105 can include at least one ultraviolet (UV) light 300. An "ultraviolet light" ("UV light") 300 is an emitter that emits electromagnetic waves in the ultraviolet wavelength range, i.e., 100-400 nm. The UV light 300 can emit UVC waves, i.e., waves having wavelengths between 100-280 nm. UV waves can destroy pathogens when provided for a prescribed duration that is based on the distance between the UV light 300 and the surface and an emission strength of the UV light 300 (i.e., an amount of UV radiation that the UV light 300 can emit) toward the target surface. Actuating the UV light 300 toward a surface can reduce pathogens (such as bacteria and viruses) on the surface. The computer 110 can actuate an ultraviolet light 300 to sanitize a surface of the vehicle 105 to reduce pathogens in the vehicle 105.

The UV light 300 includes an emitter 305 that emits the UV waves. The UV light 300 can include a motor that rotates the emitter 305 about a hemisphere. The emitter 305 can be movable along a hemisphere, i.e., one or more motors can rotate the emitter 305 about two axes to emit UV waves to surfaces of the passenger cabin 200. The emitter 305 can define an emission direction along which the UV waves travel. The computer 110 can actuate the one or more motors to rotate the emitter 305 toward one of the surfaces and can actuate the emitter 305 to emit UV waves toward the surface. The UV light 300 can be movable to emit UV waves toward substantially all surfaces of the passenger cabin 200. In another example, respective emitters 305 or two or more UV lights 300 can focus their respective UV waves on a same surface to produce a greater amount of UV light than one emitter 305 can emit, allowing the UV lights 300 to sanitize surfaces outside of an emission range of one of the UV lights 300 and/or to reduce the time required to sanitize the surface.

The vehicle 105 can include a motorized air vent 310. The passenger cabin 200 can include a plurality of air vents 310 to direct air from the climate control component 230 to the passenger cabin 200. Each vent 310 can include a respective motor to direct the air in the passenger cabin 200. The vent 310 can be movable to direct air toward an occupant. That is, the motor can rotate fins of the air vent 310 to direct heated air to a surface in the passenger cabin 200. For example, the motor can rotate the air vent 310 to direct heated air onto a vehicle seat. In another example, the motor can rotate the air vent 310 to direct heated air onto a window. In another example, the motor can rotate the air vent 310 to direct heated air onto a windshield. That is, the computer 110 can actuate the motor to direct the air from the heater 205 through the vent 310 toward an identified surface that requires sanitizing. Directing the air onto the identified surface can increase the temperature of the surface, sanitizing the surface.

The vehicle 105 can include a window heater 315. The window heater 315 can include one or more devices that provide heat to a window and/or a windshield. For example, the window heater 315 can be a wire embedded in a window that, when passing electricity therethrough, heats the surrounding glass of the window and/or the windshield. Alternatively, or additionally, the window heater 315 can be a vent in fluidic communication with a climate control component 230 blower or fan that blows heated air on the window and/or the windshield. Yet further alternatively or additionally, the window heater 315 can be infrared reflective (IRR) metalized particles disposed in the window, shown in broken lines in FIG. 3.

The computer 110 can actuate one or more of the components described above to sanitize the vehicle 105. To determine which components to actuate, the computer 110 can refer to a look-up table or the like. The look-up table can identify specific components to actuate based on an amount of heat and/or light that can reach the surface. That is, each column of the look-up table can be an amount of heat and/or light reaching the surface, as determined by the sensors 115, and each row can list one of the components to actuate. Thus, upon identifying an amount of heat and/or light reaching the surface, the computer 110 can identify the column of the look-up table corresponding to the identified amount of light and/or heat and can actuate each component identified in the column of the look-up table to sanitize the surface.

The passenger cabin 200 can include at least one mobility actuator 320 and/or portable device 135. A "mobility actuator" 320 is a device that allows actuation and mobility of the vehicle 105. The mobility actuator 320 can be, e.g., a key, a fob, a portable device 135 with an application or like to communicate with the computer 110, etc. In this context, "actuation" of the vehicle 105 means engaging the propulsion subsystem 215 to allow the vehicle 105 to move. The mobility actuator 320 and/or portable device 135 can initiate actuation and allow mobility of the vehicle 105, preparing the vehicle 105 for use by a user. For example, the mobility actuator 320 could communicate with the computer 110 over a vehicle network or communication bus to activate the vehicle 105. In another example, the portable device 135 can communicate with the computer 110 over the vehicle network or bus to activate the vehicle 105 upon receiving input from a user.

The computer 110 can identify at least one of a mobility actuator 320 (such as a key or a fob) and/or a portable device 135 (such as a phone or tablet) that can operate the vehicle 105. That is, the mobility actuator 320 and/or the or portable device 135 can actuate a lock or latch on a vehicle 105 door and/or activate the vehicle 105 upon receiving input from a user. Typically, upon identifying the mobility actuator 320 and/or portable device 135, the computer 110 can prevent the vehicle doors 225 from locking when no user is in the passenger cabin 200, preventing the user from being unable to unlock or unlatch the doors 225 because the mobility actuator 320 and/or portable device 135 is locked in the passenger cabin 200. That is, the computer 110 prevents the user from locking the mobility actuator 320 in the passenger cabin 200. To prevent entry into the vehicle 105 during the sanitizing operation, the computer 110 can suppress this lock prevention feature, allowing the doors 225 to lock while the mobility actuator 320 and/or the portable device 135 is in the passenger cabin 200. The computer 110 can notify the user, e.g., to a portable device 135 of the user, that the lock prevention feature of the mobility actuator 320 and/or the portable device 135 in the vehicle 105 is suppressed until the sanitizing operation is complete and the vehicle 105 is unlocked.

While the temperature in the passenger cabin 200 is above the sanitizing temperature, the computer 110 can suppress instructions from the mobility actuator 320 and/or portable device 135 to unlock the doors and/or move the vehicle 105. That is, while the heater 205 sanitizes the passenger cabin 200, the computer 110 prevents mobility of the vehicle 105 and/or unlocking the door 225, preventing entry into the vehicle 105. When the heater 205 finishes sanitizing the vehicle 105, the computer 110 can allow the mobility actuator 320 and/or portable device 135 to unlock the doors and/or activate the vehicle 105 when the temperature of the passenger cabin falls below a second temperature threshold, as described above.

As described above, upon identifying the mobility actuator 320 and/or portable device 135, the computer 110 can prevent the vehicle 105 doors from locking when no user is in the passenger cabin, preventing the user from being unable to unlock or unlatch the vehicle 105 doors because the mobility actuator 320 and/or portable device 135 is locked in the passenger cabin. The computer 110 can override this lock prevention upon actuating the heater 205, locking the vehicle doors 225 while the mobility actuator 320 and/or portable device 135 is in the passenger cabin 200 without the user. When the sanitizing operation is complete, the computer 110 can receive an input from, e.g., a second mobility actuator 320, a second portable device 135 external to the vehicle 105, a keypad mounted on an exterior surface of the vehicle 105, an unlock instruction from the network 125 sent from a computer external to the vehicle 105, etc., to unlock the vehicle 105. The computer 110 can unlock the vehicle 105 according to the input when the temperature of passenger cabin 200 falls below the second threshold, as described above.

The computer 110 can actuate a vehicle security subsystem 120 to deter theft of contents or prevent mobility of the vehicle 105 during sanitizing of the passenger cabin 200. The vehicle security subsystem 120 provides security for the user of the vehicle 105 by identifying and/or preventing threats to the vehicle 105 and preventing unauthorized user access to a cabin of the vehicle 105 and/or preventing the vehicle 105 from moving during the sanitizing operation. Preventing access to the vehicle 105 and mobility of the vehicle 105 while sanitizing the passenger cabin protects objects in the vehicle 105 from theft and prevents external users from disrupting the sanitizing operation and/or introducing pathogens to the vehicle 105. When the heater 205 is deactivated and the sanitizing operation is completed, the computer 110 can deactivate the vehicle security subsystem 120 to allow access to and/or mobility of the vehicle 105. That is, upon completion of the sanitizing operation, the computer 110 can return the vehicle security subsystems 120 to a default security state and allow users to use the vehicle 105.

The computer 110 can actuate a proximity motion sensor 115 to detect movement of objects within a predetermined distance from the sensor 115 during the sanitizing operation. That is, when a moving object external to the vehicle 105 moves within the predetermined distance, the proximity motion sensor 115 can identify the moving object. The predetermined distance can be determined by, e.g., a manufacturer. To detect movement, the proximity motion sensor 115 can be programmed to detect speeds of objects above one or more thresholds. For example, the proximity motion sensor 115 can be programmed to detect a speed of an object above a first threshold when the vehicle 105 is not in the sanitizing operation and above a second threshold during a sanitizing operation. The second threshold can be lower than the first threshold, i.e., the proximity motion sensor 115 can detect more objects exceeding the second threshold than exceeding the first threshold. Decreasing the threshold increases the sensitivity of the proximity motion sensor 115, increasing the number of objects detected. Increasing the number of objects detected improves the security of the vehicle 105 by identifying additional objects that could interrupt the sanitizing operation.

The computer 110 can suppress a proximity motion sensor 115 in an interior of the vehicle 105 during the sanitizing operation. That is, the vehicle 105 can include one or more proximity motion sensors 115 in the interior of the vehicle 105 programmed to detect objects moving in the vehicle 105. To "suppress" the proximity motion sensor 115 means to decrease sensitivity of the proximity motion sensor 115 (e.g., by increasing a speed threshold described above) and/or to deactivate the proximity motion sensor 115. The computer 110 can disregard data from the proximity motion sensors 115 related to detection of motion of objects within the cabin as a precaution against false triggers which could result from vibration of objects in the passenger cabin 200 caused by operation of the propulsion subsystem 215 of the vehicle 105 to generate power for the sanitizing operation.

The computer 110 can actuate a camera 115 that can detect objects external to the vehicle 105. That is, the camera 115 can collect one or more images and the computer 110 can use a conventional object-detection algorithm (e.g., Canny edge detection, deep learning object detection, etc.) to identify one or more objects external to the vehicle 105. The camera 115 can record video data, i.e., sequences of images at a specified frame rate (e.g., 24 frames per second) of the objects external to the vehicle. The computer 110 can upload the video data to the server 130 for, e.g., diagnostic and/or regulatory analysis.

The computer 110 can provide output to notify users that the sanitizing operation is occurring and can further notify users of objects that could interfere with the sanitizing operation. Notifying users that the sanitizing operation is occurring can prevent users from inadvertently disturbing the sanitizing operation and/or introducing pathogens to the vehicle 105. For example, upon identifying an object with a proximity motion sensor 115 and/or a camera sensor 115, the computer 110 can provide output indicating that an object is proximate. In another example, the computer 110 can provide output upon actuating the heater 205. In another example, if a user touches, e.g., grasps, a door latch 220 during the sanitizing operation, the computer 110 can provide output.

The notification output can include at least one of an audio, visual, and/or haptic output. For example, the computer 110 can actuate a speaker to play a siren. In another example, the computer 110 can actuate one or more headlights in a periodic, flashing pattern. In another example, the computer 110 can actuate a vehicle horn. In another example, the computer 110 can provide an audio message through the speaker to warn the user that the sanitizing operation is occurring.

The computer 110 can identify and classify an object in the passenger cabin 200. To "classify" an object is to assign a type or class to an object. For example, the computer 110 can classify an object in the passenger cabin as "electronic device" or "luggage" or "frozen groceries." Some objects may be damaged when heated by the heater 205, e.g., frozen groceries may thaw. In one example, an object so classified could be an animate or inanimate object. To prevent damage to heat-sensitive objects, the computer 110 classifies the objects and determines whether, based on the classification, objects that may be damaged when heated by the heater 205. The computer 110 can identify and classify the object with a conventional image-recognition technique, e.g., Canny edge detection, deep machine learning, etc., with a camera and/or a thermal sensor 115, whereby an object can be detected in an image and classified. Based on the classification, the computer 110 can prevent actuation of the heater 205. For example, if the classification of the object is an "electronic device" that may be damaged by the temperature required to sanitize the passenger cabin, the computer 110 can prevent actuation of the heater 205 and output a message to the user that the object classified as "electronic device" is in the passenger cabin 200.

Criteria to Initiate Sanitizing Operation

The computer 110 can receive input to begin, i.e., initiate, a sanitizing operation. For example, a user can provide input to, e.g., a portable device 135 in communication with the computer 110 via the network 125 and/or a via wired or wireless connection, e.g., Bluetooth® or the like. Alternatively, or additionally, a user can provide the input to a vehicle human-machine interface (HMI), e.g., a touchscreen display such as an in-cabin, phone, or Internet-based HMI, a numeric keypad disposed on a vehicle door 225, etc.

The computer 110 can sanitize the vehicle 105 based on a current location of the vehicle 105. The "location" of the vehicle 105 is a set of geo-coordinates at which the vehicle 105 is located. Use of one or more components and/or devices such as may be selected for sanitizing may be prohibited, e.g., according to local regulations. For example, a certain location may disallow remote operation of a heater 205 to comply with noise regulations, such as a remote start operation of the propulsion subsystem 215. In another example, a certain location may disallow certain heaters 205, e.g., that burn combustible fuels, to comply with air quality regulations. The computer 110 can actuate components to perform the sanitizing operation that comply with all regulations in effect at the location of the vehicle 105. Additionally, the computer 110 can receive an instruction from the server 130 to actuate one or more components that may typically be restricted by the regulations in effect at the location of the vehicle 105 upon approval by local municipal authorities.

The computer 110 can identify an insolation of a location of the vehicle 105. In this context, "insolation" is an amount of solar radiation in a specified geographic area and can be measured in Watts per square meter (W/m$^2$). The computer 110 can predict the insolation at the location based on, e.g., insolation models, a time of day, a current date, weather forecast data, vehicle orientation, etc. The insolation can increase the temperature in the passenger cabin 200 as the insolation passes through the windows and windshield of the vehicle 105. That is, based on conventional insolation thermal models that use the Stefan-Boltzmann temperature law $j=\varepsilon\sigma T^4$, where j is the insolation data, the computer 110 can determine an increase in temperature T of the passenger cabin 200 caused by the insolation j. As described above, electromagnetic waves j can be emitted by a surface at a temperature T according to the Stefan-Boltzmann temperature law, and absorbed electromagnetic waves j can increase a temperature of a surface according to the Stefan-Boltzmann temperature law. That is electromagnetic waves j from the sun (i.e., insolation) can, based on the thermal models, increase the temperature in the passenger cabin 200 relative to the ambient external temperature, and the computer 110 can actuate the heater 205 to heat the passenger cabin 200 from this increased temperature to a sanitizing temperature. Alternatively, or additionally, the computer 110 can use a machine learning program (e.g., a deep neural network, a gradient boosted tree, etc.) trained to receive inputs of a location, a time of day, a current date, and/or weather data, and to output the insolation. The machine learning program can be trained using, e.g., sets of training data including specified locations, times of day, dates, and weather annotated with the insolation, and a cost function of the machine learning program can be minimized to train the machine learning program to output the insolation.

The insolation data can include a direction of the highest insolation, that is, a direction along which the rays from the sun have a greatest intensity, i.e., a highest Watts per square meter. That is, the direction of the highest insolation can be included in the insolation data based on the current time and the location of the vehicle 105, i.e., the solar radiation defines an angle with the ground based on the latitude at which the vehicle 105 is located and the current time of day. This angle, i.e., the direction of highest insolation, can be determined with, e.g., conventional solar radiation models, a sensor 115 programmed to collect insolation data, etc. The computer 110 can, upon identifying the direction of highest insolation, move the vehicle 105 to align the identified surface with the direction of highest insolation. That is, the computer 110 can move the vehicle 105 so that the identified surface is along the direction of highest insolation, receiving the most insolation compared to any other orientation of the vehicle 105. For example, the computer 110 can determine an angle of incidence between the insolation and the surface by comparing the direction of highest insolation and image data of the surface. The computer 110 can determine an orientation of the vehicle 105 that adjusts the angle of incidence closest to a vector normal to the surface by rotating a virtual model of the vehicle 105 until the direction of highest insolation is normal to the surface. That is, when the insolation is normal to the identified surface, the highest amount of irradiance from the insolation contacts the identified surface compared to other angles of incidence, increasing the insolation absorbed by the surface and thus increasing the temperature of the surface. The computer can then move the vehicle 105 to position a surface to be as aligned as closely as possible, given constraints of the physical world, with the highest insolation predicted by the virtual model.

Alternatively, or additionally, the computer 110 can output a message to a user with instructions to move the vehicle 105 to align the identified surface with the direction of highest insolation. When the insolation reaches the surface, the insolation increases the temperature of the surface, sanitizing the surface. Yet alternatively, or additionally, the computer 110 can move the vehicle 105 so that solar radiation along the direction of highest insolation enters through an east-facing window when the current time is before noon and the solar radiation along the direction of highest insolation enters through a west-facing window when the current time is after noon. That is, the computer 110 can determine an orientation of the vehicle 105 relative to the direction of highest insolation that accounts for the western movement of the sun and the changes in the direction of highest insolation as the sun moves westward along the sky.

The computer 110 can identify an ultraviolet irradiance of the insolation data, i.e., an amount of UV waves in the insolation, typically measured in Watts per square meter. That is, the insolation data can include data about wavelengths of the insolation, and the computer 110 can determine an intensity (measured in Watts per square meter) of radiation having wavelengths in the UV range, i.e., 100-400 nm as described above. The computer 110 can open one or more windows when the ultraviolet irradiance of insolation data collected by one or more sensors 115 exceeds an irradiance threshold. The irradiance threshold can be determined based on, e.g., empirical testing of UV irradiance reducing pathogens. That is, empirical testing can include test vehicles 105 that are irradiated with UV waves during the sanitizing operation. The testing can determine the amount of irradiance at which the number of pathogens reduced by the UV irradiance exceeds the number of pathogens reduced by air heated by the heater 205. This amount of irradiance can be the irradiance threshold. Alternatively, or additionally, the computer 110 can adjust a tint and/or images in an integrated display to increase the transparency of the window, allowing insolation that would be typically blocked by the tint and/or the images of the integrated display to enter the passenger cabin 200.

The computer 110 can predict an amount of energy use to heat the passenger cabin 200 above the temperature threshold. That is, actuating the components uses energy from the battery and/or liquid fuel, and the computer 110 can predict the amount of electricity from the battery and/or the amount of fuel required to heat the passenger cabin 200. The computer 110 can predict the amount of energy used based on a predicted amount of power provided to the heater and a predicted duration time of actuation of the heater 205. The computer 110 can predict the amount of power provided to the heater 205 based on, e.g., a heater specification, empirical testing of heaters and test vehicles 105, actual or predicted insolation, etc. That is, the computer 110 can use the heater specification to determine an amount of energy used by the heater 205 for the duration time to increase the temperature of the passenger cabin 200 to the sanitizing temperature. The computer 110 can predict the duration time of actuation of the heater 205 based on, e.g., thermal models, insolation, empirical testing of test vehicles 105, etc. The computer 110 can predict the amount of fuel required to heat the passenger cabin 200 based on, e.g., thermal models, insolation, empirical testing of test vehicle 105, etc.

Upon predicting the amount of energy use, the computer 110 can determine an energy level of the vehicle 105. An "energy level" of the vehicle 105 is a current volume of fuel or battery charge of the vehicle 105, e.g., available on a vehicle 105 communications bus from one or more sensors 115. In some examples, a vehicle 105 includes a first energy level and a second energy level, e.g., a first energy level of liquid fuel and a second energy level specifying a state of charge of a battery or batteries. For example, the computer 110 can actuate a sensor 115 to detect a volume of fuel in a fuel tank and/or a second sensor 115 to detect a charge of a vehicle battery. The volume of fuel and/or the charge of the vehicle battery can be the "energy level." That is, the heater 205 may use liquid fuel from the fuel tank and/or electric energy from the battery to heat the passenger cabin 200, and the propulsion subsystem 215 can restore electric energy to the battery using liquid fuel to rotate, e.g., an alternator. Thus, an energy level of the vehicle 105 can include one or two values: the volume of fuel and the charge of the vehicle battery. The computer 110 can receive the volume of fuel and the charge of the vehicle battery from one or more sensors 115, as described above. The computer 110 can output to a user device or HMI the energy level of the vehicle 105 determined from the sensor 115 data and the predicted amount of energy use to heat the passenger cabin 200. The computer 110 can also output to a user device or HMI the amount of power and/or fuel provided to the heater 205 and the duration time of actuation of the heater 205. The computer 110 can compare the energy level determined from the sensors 115 to the predicted amount of energy to be used to perform the sanitizing operation. If the predicted amount of energy use exceeds the energy level of the vehicle 105, the computer 110 can output a message to the user device or HMI that the sanitizing operation cannot be performed because the energy level of the vehicle 105 is insufficient to perform the sanitizing operation.

When the temperature of the passenger cabin 200 exceeds the threshold, the computer 110 can output a message to a second computer that the temperature of the passenger cabin 200 exceeds the threshold. For example, the computer 110 can output the message to the portable device 135 of the user that the passenger cabin 200 has reached the sanitizing temperature. In another example, the computer 110 can output the message to the server 130, and the user can access the server 130 from, e.g., the portable device 135 for the output that the sanitizing temperature has been reached.

The computer 110 can predict a time period for the passenger cabin 200 to cool from the sanitizing temperature to a second temperature below a second threshold. Upon sanitizing the vehicle 105, the computer 110 can determine when the vehicle 105 will cool enough to be occupied by a human. That is, the second threshold can be a predetermined value at which the vehicle 105 is sufficiently cooled for human occupancy. For example, the second threshold can be, e.g., 80 degrees Fahrenheit. In another example, the second threshold can be the ambient temperature of the air around the vehicle 105, as described above. The computer 110 can predict the time period based on conventional thermal models such as a conduction heat transfer model that receives the temperature of the passenger cabin 200 and the second threshold as input and outputs the time for the temperature of the passenger cabin 200 to decrease to the second threshold.

The computer 110 can determine whether the vehicle 105 has been used by another user since a previous sanitizing operation was performed. If another user has used the vehicle 105 since a previous sanitizing operation was performed, the other user may have introduced pathogens into the vehicle 105, and the user and/or the computer 110 can determine to perform the sanitizing operation. If no user has used the vehicle 105 since the passenger cabin 200 was previously heated to above the temperature threshold, and the passenger cabin 200 is secure (i.e., all doors, windows, and sun roof, if present, are in respective closed positions), the computer 110 can output that the vehicle 105 has not been used since the last sanitizing operation. The user can provide input not to actuate the heater 205. Alternatively, or additionally, the computer 110 determine not to initiate the sanitizing operation if no user has used the vehicle 105 since the passenger cabin 200 was previously sanitized.

Upon completing the sanitizing operation, the computer 110 can transmit data to the server 130 about the sanitizing operation. The data can include, e.g., a date and time at which the sanitizing operation initiated, a time at which the sanitizing operation completed, a location (e.g., geo-coordinates) of the vehicle 105 during the sanitizing operation, an elapsed time of the sanitizing operation, a maximum temperature of the passenger cabin 200 during the sanitizing operation, the criteria that caused initiation of the sanitizing operation, criteria ending the sanitizing operation, etc. The data in the server 130 about the sanitizing operation can be used for, e.g., statistical analysis by a manufacturer about sanitizing operations of vehicles 105, regulatory compliance for municipalities, etc.

Initiation Time of Sanitizing Operation

Upon receiving input to initiate sanitization, the computer 110 can determine one or more candidate initiation times to actuate one or more heaters 205 to sanitize the passenger cabin 200. An "initiation time" is a time at which the computer 110 actuates a heater 205 and/or a UV light 300 to initiate the sanitizing operation. A "candidate" initiation time is a proposed initiation time that can be confirmed by input to the computer 110, e.g., via a portable device 135. The candidate initiation times can include, e.g., a current time to immediately begin heating the passenger cabin 200. The computer 110 can output the candidate initiation times for display on a vehicle HMI or, more typically, a portable device 135. A second input, e.g., provided by a user via a device 135, can identify one of the initiation times. The computer 110 can initiate the sanitizing operation at the identified initiation time.

Input to initiate a sanitizing operation can include a time of next use for the vehicle 105. That is, the user can provide the computer 110 with an upcoming time at which the user plans to operate the vehicle 105, i.e., a specified "time of next use." The computer 110 can identify the candidate initiation times as times prior to the time of next use. That is, to finish sanitizing the vehicle 105 prior to the time of next use, the computer 110 can identify the candidate initiation times as times that are at least the time threshold prior to the time of next use. For example, the candidate initiation times can be at least 15 minutes prior to the time of next use. Alternatively, or additionally, the computer 110 can identify one of the candidate initiation times as a time of predicted maximum insolation prior to the time of next use.

Input to initiate the sanitizing operation can include a predicted insolation, as described above. For example, the computer 110 can determine a maximum predicted insolation, i.e., a time at which the insolation is predicted to be highest on a specific day. One of the candidate initiation times can be the time at which the maximum predicted insolation is predicted to occur.

The computer 110 can determine the candidate initiation times based on whether the vehicle 105 is in an enclosed space, as described above. If the vehicle 105 is in an enclosed space, operation of the vehicle 105 may be limited to a specified time period to reduce exhaust accumulation from an internal combustion engine. If the computer 110 determines that the time to complete the sanitizing operation would exceed the specified time period, the computer 110 can request the user to move the vehicle 105 out from the enclosed space.

The computer 110 can determine one of the candidate initiation times such that the predicted time period for the passenger cabin 200 to cool from the sanitizing temperature to a second temperature below a second threshold would elapse prior to the time of next use provided by the user, allowing the sanitizing operation to complete prior to the time of next use. The computer 110 can output the time period to the user, e.g., to the portable device 135. If the user determines that the time period would extend past a planned time of next use, the user can provide second input not to sanitize the vehicle 105.

The computer 110 can output a message to the user with the candidate initiation times, as described above. Additionally, the computer 110 can include data described above in the message, e.g., the identified objects, the ambient temperature data, the insolation data, etc. Based on the additional data, the user can provide the second input indicating one of the candidate initiation times. For example, the user can select one of the initiation times based on the predicted energy use to perform the sanitizing operation. When the computer 110 receives the selected initiation time, the computer 110 initiates the sanitizing operation at the selected initiation time.

Based on the selected initiation time, the computer 110 can extend a previously determined operation time of the vehicle 105. When the computer 110 is not performing the sanitizing operation, the computer 110 can deactivate the vehicle 105 after a predetermined period of time without input from the user. The predetermined period of time is an "operation time," and can be determined to maintain a specified energy level, as described above, for the next use of the vehicle 105. For example, the operation time can be 15 minutes for a vehicle 105 with a fully electric propulsion subsystem 215. In another example, the operation time can be 60 minutes for a vehicle 105 with an internal combustion engine. If the operation time elapses during the sanitizing operation, the computer 110 can extend the operation time until the sanitizing operation completes, deactivating the vehicle 105 only after completion of the sanitizing operation.

Processing

Figure 4:
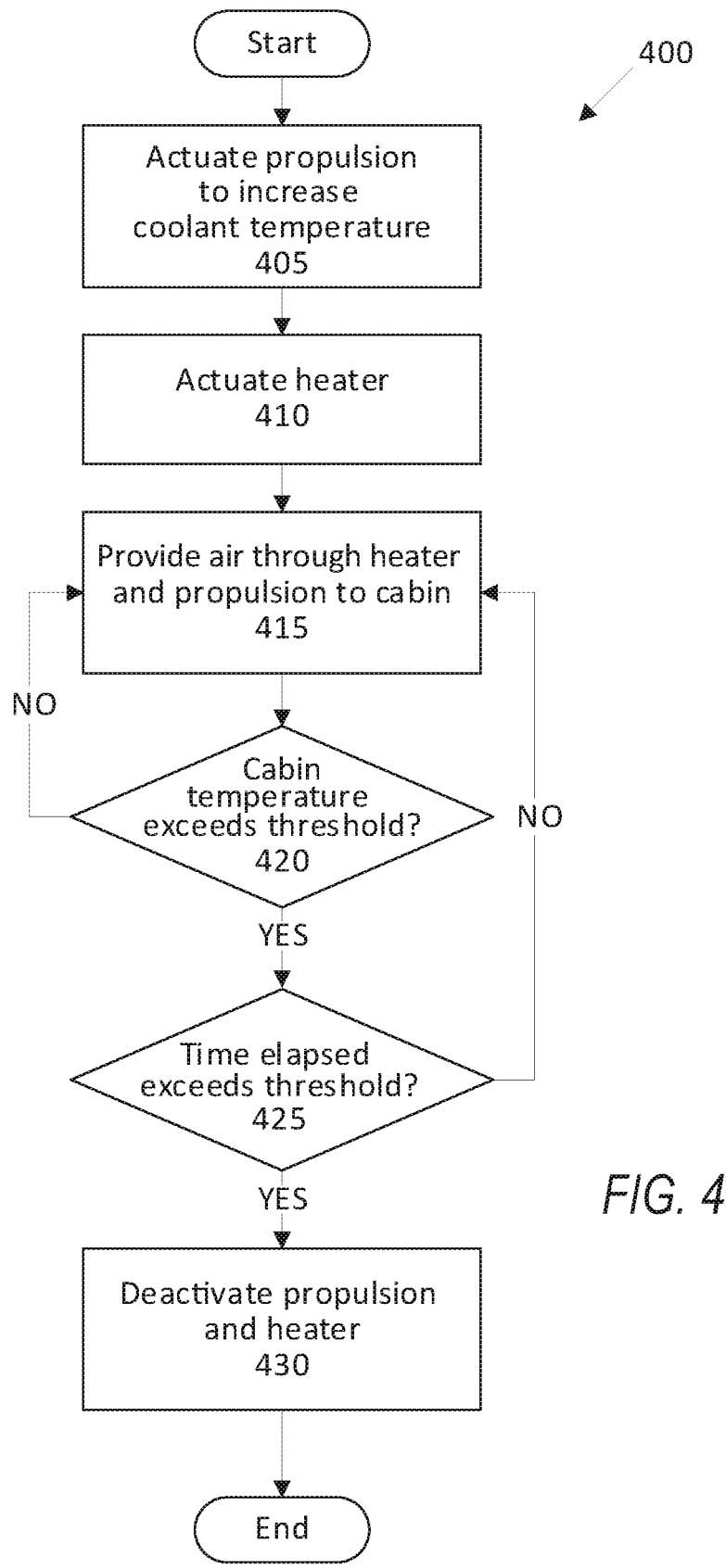
FIG. 4 is a diagram of an example process for heating the vehicle of FIG. 2.

FIG. 4 is a diagram of a process 400 for sanitizing a vehicle 105. The process 400 begins in a block 405, in which a computer 110 of the vehicle 105 actuates a propulsion subsystem 215 to increase a temperature of engine coolant. As described above, a climate control component 230 can use heated engine coolant to increase a temperature of a passenger cabin 200 of the vehicle 105.

Next, in a block 410, the computer 110 actuates a heater 205. The heater 205 can be part of the climate control component 230, e.g., a resistive coil heater. Alternatively, or additionally, the heater 205 can be a separate component in the passenger cabin 200 of the vehicle 105. The heater 205 can increase the temperature of the passenger cabin 200. That is, a working fluid such as air can pass over the heater

205, heating the air and transferring heat from the heater 205 to the passenger cabin 200. In the example of FIG. 4, both the propulsion subsystem 215 and the heater 205 provide heat to the passenger cabin 200 in blocks 405 and 410. Alternatively, one of blocks 405 or 410 can be omitted, i.e., the computer 110 can actuate one of the heater 205 or the propulsion subsystem 215.

Next, in a block 415, the computer 110 provides air through the heater 205 and/or the propulsion subsystem 215 to heat the passenger cabin 200. As described above, the climate control component 230 can include an air blower 235 to move air past the engine coolant and/or the heater 205, transferring heat from the engine coolant and/or the heater 205 to the passenger cabin 200. For example, the climate control component 230 can include one or more heat exchangers to transfer heat from the engine coolant and/or the heater 205 to the air.

Next, in a block 420, the computer 110 determines whether the temperature of air in the passenger cabin 200 exceeds a temperature threshold. As described above, the temperature threshold can be a sanitizing temperature, i.e., a temperature at which specified pathogens are reduced by a specified amount. For example, according to data from the World Health Organization (WHO) about Severe Acute Respiratory Syndrome (SARS) coronavirus survivability, the temperature threshold can be 133 degrees Fahrenheit (55 degrees Celsius) to kill 10000 viruses. If the temperature of the air in the passenger cabin 200 exceeds the threshold, the process 400 continues in a block 425. Otherwise, the process 400 returns to the block 415 to provide more heated air to the passenger cabin 200.

Next, in a block 425, the computer 110 determines whether an elapsed time that the temperature of the passenger cabin 200 has been above the threshold exceeds a time threshold. As described above, the time threshold can be a time at which a specified amount of pathogens are reduced. For example, according to the WHO data above, the time threshold can be 15 minutes to kill 10000 viruses. If the elapsed time exceeds the threshold, the process 400 continues in a block 430. Otherwise, the process 400 returns to the block 415 to provide more heated air to maintain the temperature of the passenger cabin 200 above the temperature threshold.

In the block 430, the computer 110 deactivates the heater 205 and the propulsion subsystem 215. Deactivating the heater 205 and the propulsion subsystem 215 allows the passenger cabin 200 to cool to a temperature usable by a user, e.g., 80 degrees Fahrenheit. That is, upon sanitizing the vehicle 105, the computer 110 can cease heating the passenger cabin 200. Following the block 430, the process 400 ends.

Figure 5:
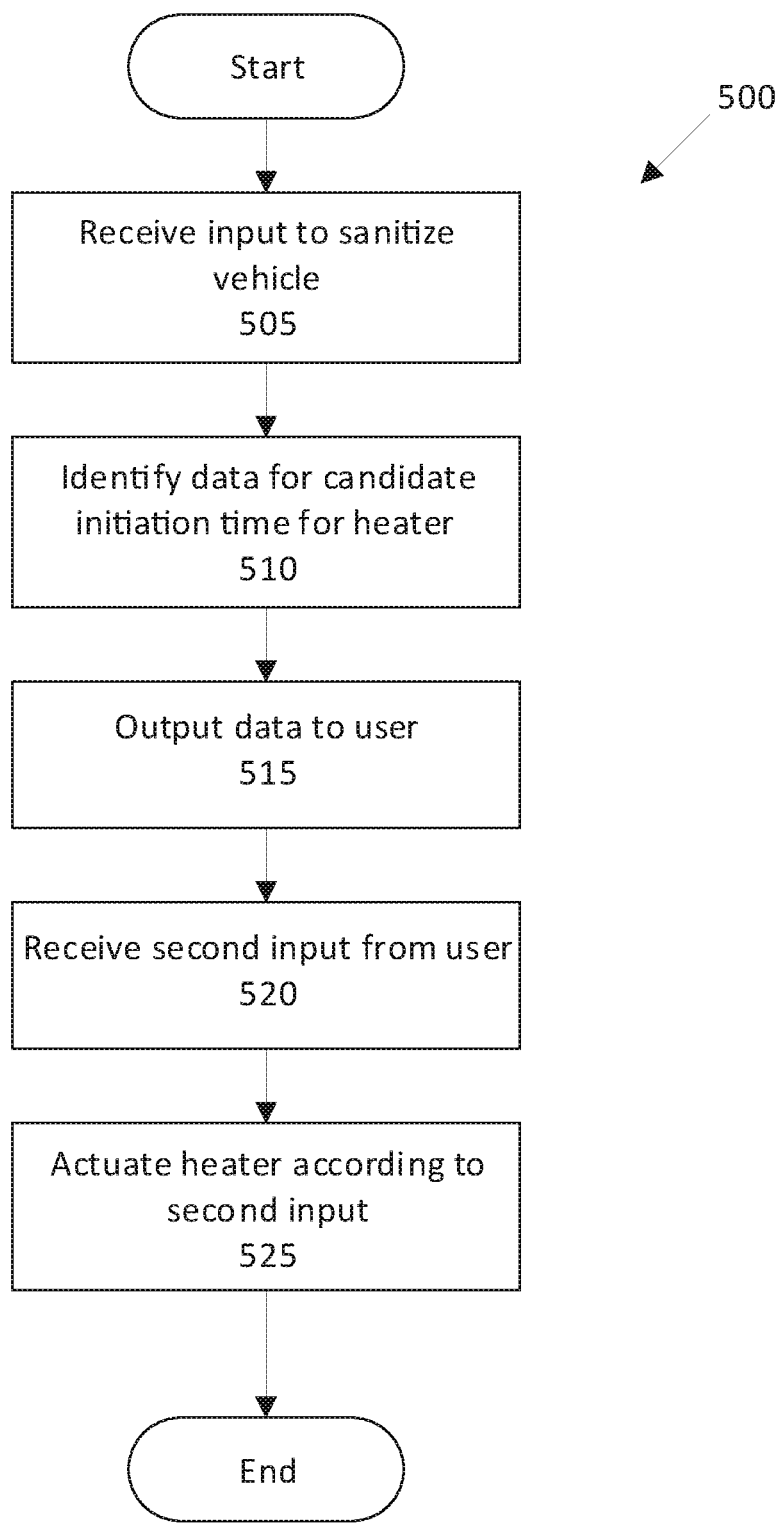
FIG. 5 is a diagram of an example process for determining an initiation time to heat the vehicle of FIG. 2.

FIG. 5 is a diagram of an example process 500 for determining an initiation time to heat a vehicle 105. The process 500 begins in a block 505, in which a computer 110 in the vehicle 105 receives input from an external portable device 135 to sanitize the vehicle 105. A user of the vehicle 105 can provide input to the portable device 135 instructing the computer 110 to sanitize the vehicle 105, and the portable device 135 can transmit the input over the network 125 to the computer 110.

Next, in a block 510, the computer 110 determines one or more candidate initiation times to initiate a heater to begin sanitizing the vehicle 105. The computer 110 can determine the candidate initiation times based on data collected in the vehicle 105. For example, the computer 110 can determine an insolation of the location at which the vehicle 105 is located and can select one of the candidate initiation times based on a time at which the insolation is highest. Additionally, or alternatively, the computer 110 can predict an amount of energy use required to sanitize the vehicle 105 and can select one of the candidate initiation times based on the predicted amount of energy use.

Next, in a block 515, the computer 110 outputs the candidate initiation times to the user. The computer 110 can send a message to the portable device 135 over the network 125 with the candidate initiation times. The message can include additional data, e.g., a predicted amount of energy use, a predicted time for the passenger cabin 200 to cool after completing the sanitizing operation, etc. Input to the portable device 135 can, based on the additional data, select one of the candidate initiation times, as described above.

Next, in a block 520, the computer 110 receives a second input from the portable device 135. The second input can include a selection of one of the candidate initiation times. Alternatively, the second input can include a command to cease the sanitizing operation.

Next, in a block 525, the computer 110 can actuate a heater 205 to heat the vehicle 105 according at the selected initiation time. The computer 110 can heat the passenger cabin 200 above the temperature threshold for an elapsed time exceeding a time threshold, as described above, to sanitize the vehicle 105. When the elapsed time exceeds the time threshold, the computer 110 can deactivate the heater 205. Following the block 525, the process 500 ends.

Figure 6:
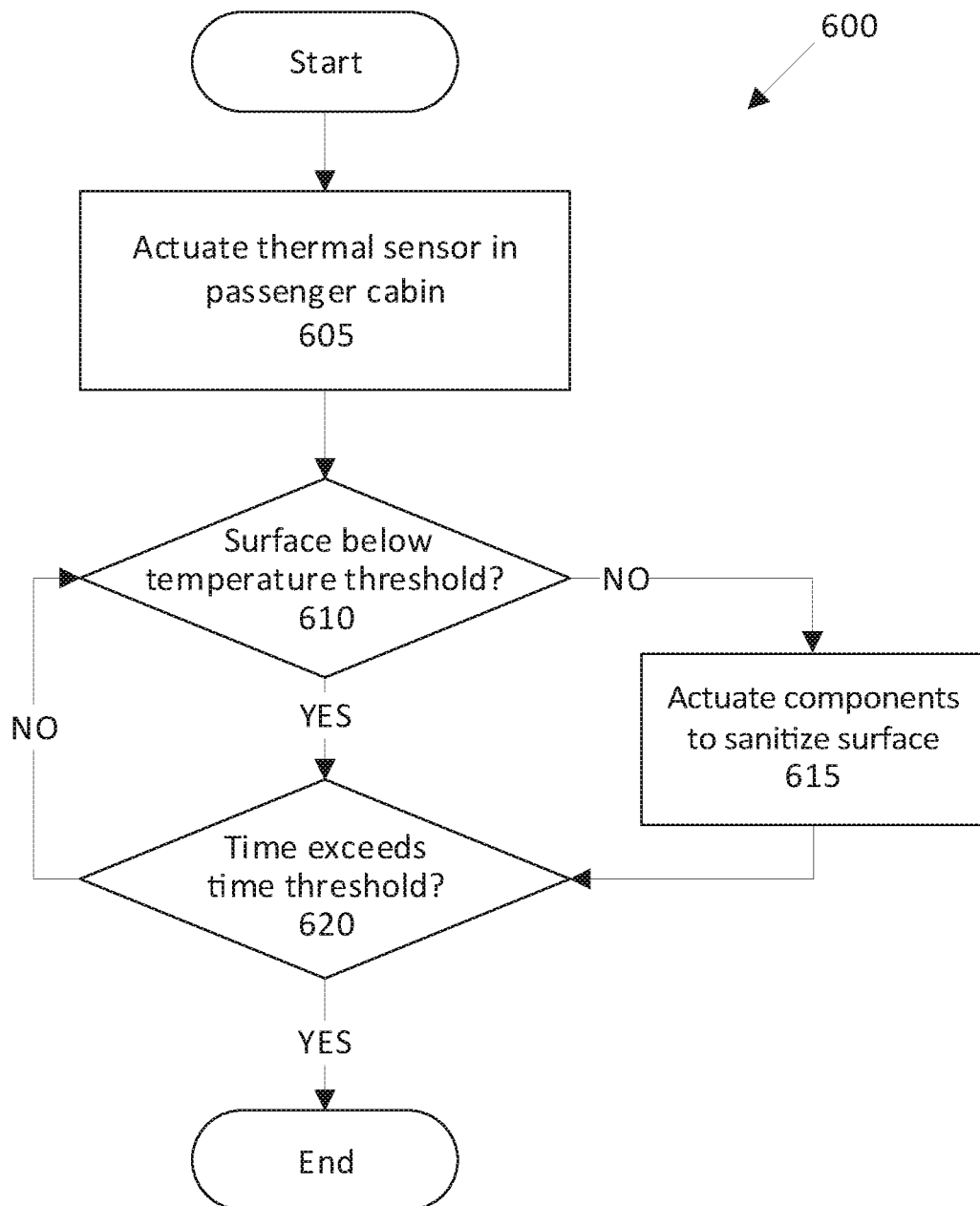
FIG. 6 is a diagram of an example process for sanitizing a surface in a vehicle.

FIG. 6 is a block diagram of an example process 600 for sanitizing a surface in a vehicle 105. The process 600 begins in a block 605, in which a computer 110 of the vehicle 105 actuates a thermal sensor 115 in the passenger cabin 200. As described above, the thermal sensor 115 detects temperatures of surfaces in the passenger cabin 200. The computer 110 can actuate the thermal sensor 115 when a temperature of air in the passenger cabin 200 exceeds a temperature threshold, e.g., a sanitizing temperature as described above.

Next, in a block 610, the computer 110 determines whether the data from the thermal sensor 115 indicate a surface in the passenger cabin 200 that is below the temperature threshold. As described above, a surface in the passenger cabin 200 can be below the temperature threshold, and the computer 110 can identify the surface as the area of the surface below the temperature threshold. If the computer 110 identifies a surface below the temperature threshold, the process 600 continues in a block 615. Otherwise, the process 600 continues in a block 620.

In the block 615, the computer 110 actuates one or more components to sanitize the surface as described above. For example, the computer 110 can actuate an ultraviolet light 300 to direct ultraviolet electromagnetic waves to the surface. Additionally, or alternatively, the computer 110 can actuate a motor in an air vent 310 to direct heated air to the surface. Additionally, or alternatively, the computer 110 can actuate a window heater 315 to heat glass of a window. Additionally, or alternatively, the computer 110 can identify a direction of maximum insolation and can move the vehicle 105 so that the surface is along the direction of maximum insolation. As described above, the computer 110 can refer to a look-up table or the like to identify which of the one or more components to actuate to sanitize the surface based on an amount of heat and/or light that can reach the surface.

In the block 620, the computer 110 determines whether an elapsed time has exceeded a time threshold. As described above, upon sanitizing the surfaces below the temperature threshold and the elapsed time that the temperature of the passenger cabin 200 exceeds the temperature threshold exceeds the time threshold, the computer 110 can determine that the passenger cabin 200 is sanitized. If the elapsed time exceeds the time threshold, the process 600 ends. Otherwise, the process 600 returns to the block 610.

Figure 7:
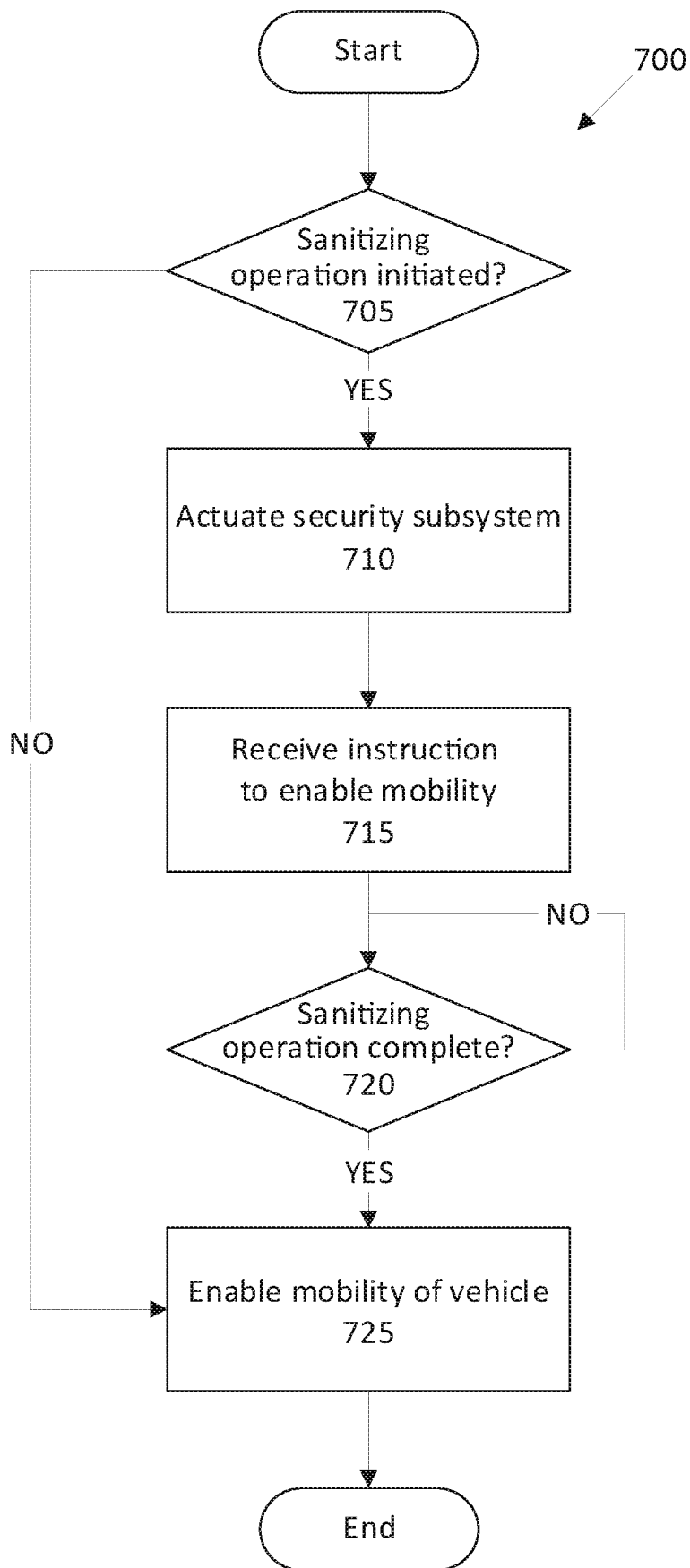
FIG. 7 is a diagram of an example process for actuating a security subsystem in the vehicle of FIG. 2.

FIG. 7 is a diagram of an example process 700 actuating a security subsystem 120 of a vehicle 105. The process 700 begins in a block 705, in which a computer 110 of the vehicle 105 determines whether there has been a request to initiate a sanitizing operation. As described above, the computer 110 can receive a request to initiate a sanitizing operation to sanitize the passenger cabin 200. For example, the computer 110 can receive the request from a portable device 135 of a user of the vehicle 105. If the sanitizing operation is initiated, the process 700 continues in a block 710. Otherwise, the process 700 continues in a block 725.

In the block 710, the computer 110 actuates one or more vehicle security subsystems 120. As described above, a "vehicle security subsystem" 120 is a component or device that performs an action to prevent access to the passenger cabin 200 and/or prevent mobility of the vehicle 105. For example, the computer 110 can actuate an internal lock on a door latch 220 of a vehicle door 225. In another example, the computer 110 can restrict a transmission 210 to a park mode. In another example, the computer 110 can deactivate an identified mobility actuator 320 in the passenger cabin 200. In another example, the computer 110 can actuate a proximity motion sensor 115 and/or a camera 115 to detect objects near the vehicle 105.

Next, in a block 715, the computer 110 receives an instruction to enable mobility the vehicle 105 has been received. A user can provide input to a portable device 135 to allow mobility the vehicle 105. As described above, "mobility" is the ability for the vehicle 105 to move from a current position, e.g., by the transmission 210 transferring output from the propulsion subsystem 215 to the wheels. That is, the user can provide input to allow the vehicle 105 to move from its current position. The portable device 135 can transmit the input over the network 125 to the computer 110.

Next, in a block 720, the computer 110 determines whether the sanitizing operation is complete. As described above, the computer 110 can determine that the sanitizing operation is complete when a temperature of the passenger cabin 200 exceeds a temperature threshold for an elapsed time exceeding a time threshold. If the sanitizing operation is complete, the process 700 continues in the block 725. Otherwise, the process 700 remains in the block 720.

In the block 725, the computer 110 enables mobility of the vehicle 105. As described above, the computer 110 can allow the transmission 210 to transfer output from the propulsion subsystem 215 to the wheels to allow mobility of the vehicle 105. The computer 110 can return the vehicle security subsystems to a default security state. For example, the computer 110 can change a threshold of a proximity motion sensor 115 to a default threshold. Following the block 725, the process 700 ends.

Figure 8:
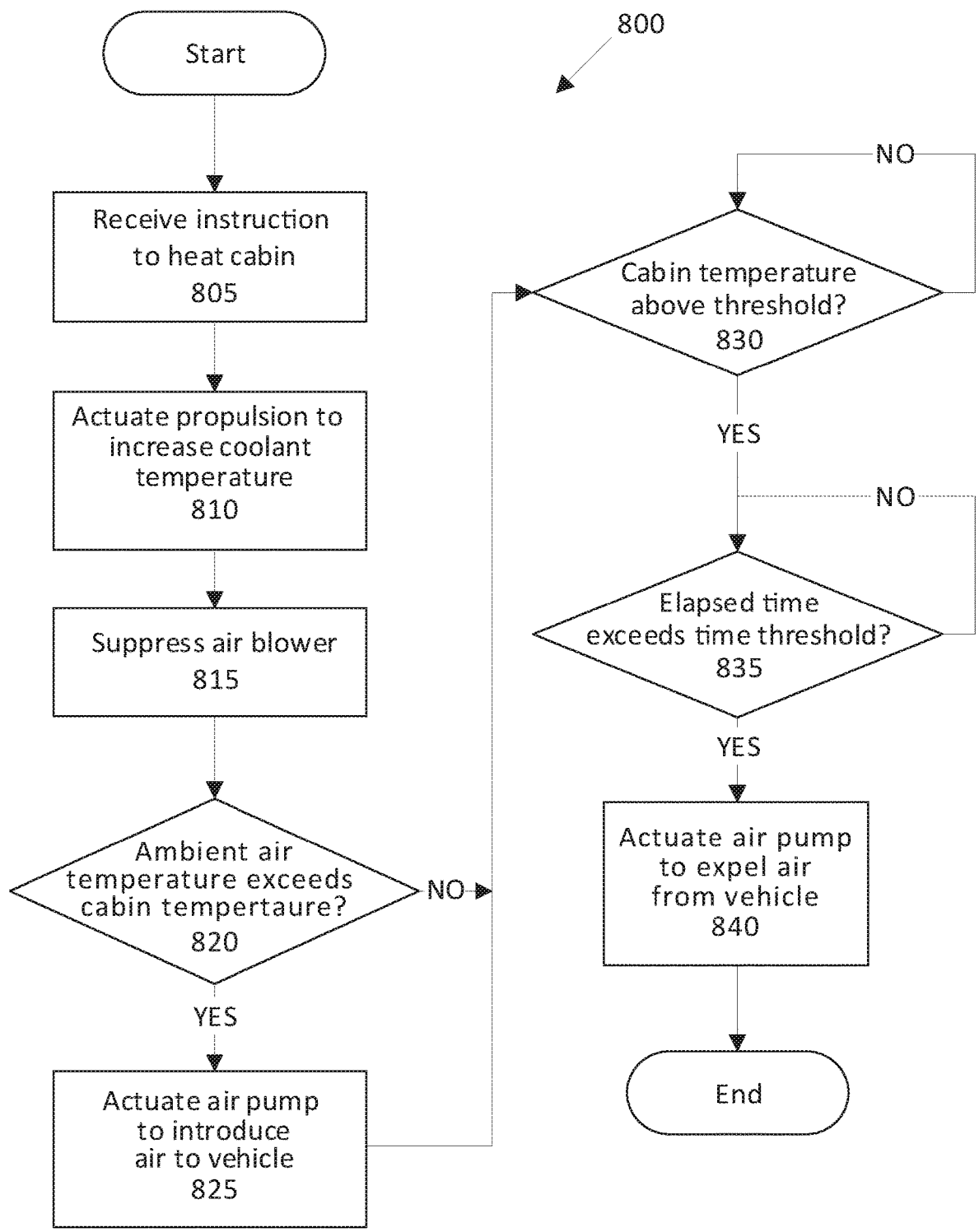
FIG. 8 is a diagram of an example process for operating a climate control component of the vehicle of FIG. 2.

FIG. 8 is a diagram of an example process 800 for operating a climate control component 230 of a vehicle 105. The process 800 begins in a block 805, in which a computer 110 receives an instruction to heat a passenger cabin 200. As described above, the computer 110 can receive an instruction to begin a sanitizing operation by heating the passenger cabin 200 to a temperature above a temperature threshold.

Next, ion a block 810, the computer 110 actuates a propulsion subsystem 215 to increase a temperature of engine coolant. As described above, the engine coolant can provide heat to heat the passenger cabin 200. The climate control component 230 can use heat from the engine coolant to heat the passenger cabin 200.

Next, in a block 815, the computer 110 suppresses an air blower 235 of the climate control component 230. As described above, the air blower 235 prevents introduction of air external to the vehicle 105 to heat the vehicle 105 when a temperature of the ambient air exceeds the temperature of the passenger cabin 200. By suppressing the air blower 235, the computer 110 can introduce air external to the vehicle 105 to heat the passenger cabin 200.

Next, in a block 820, the computer 110 determines whether the temperature of the ambient air exceeds the temperature of the passenger cabin 200. As described above, introducing ambient air that exceeds the temperature of the passenger cabin 200 can heat the passenger cabin 200 more quickly than heating the air in the passenger cabin 200. If the ambient air temperature exceeds the temperature of the passenger cabin 200, the process 800 continues in a block 825. Otherwise, the process 800 continues in a block 830.

In the block 825, the computer 110 actuates an air pump 240 to introduce air external to the vehicle 105 to the passenger cabin 200. The air pump 240 can be, e.g., a motorized extractor that pumps external air into the vehicle 105. The air pump 240 can introduce the air to the heater 205 and/or the propulsion 215, heating the air.

In the block 830, the computer 110 determines whether the temperature of the passenger cabin 200 exceeds a temperature threshold. As described above, the temperature threshold can be a sanitizing temperature. If the temperature of the passenger cabin 200 exceeds the temperature threshold, the process 800 continues in a block 835. Otherwise, the process 800 remains in the block 830.

In the block 835, the computer 110 determines whether an elapsed time since the temperature of the passenger cabin 200 exceeded the temperature threshold exceeds a time threshold. As described above, the time threshold can be a time to eliminate a specified amount of pathogens. If the elapsed time exceeds the time threshold, the process 800 continues in a block 840. Otherwise, the process 800 remains in the block 835.

In the block 840, the computer 110 actuates the air pump 240 to expel the air from the passenger cabin 200. The air pump 240 can remove the heated air from the passenger cabin 200 and out of the vehicle 105. Expelling the air from the passenger cabin 200 cools the passenger cabin by replacing the heated air with colder ambient air. Following the block 840, the process 800 ends.

Computing devices discussed herein, including the computer 110, include processors and memories, the memories generally each including instructions executable by one or more computing devices such as those identified above, and for carrying out blocks or steps of processes described above. Computer-executable instructions may be compiled or interpreted from computer programs created using a variety of programming languages and/or technologies, including, without limitation, and either alone or in combination, Java™, C, C++, Visual Basic, Java Script, Python, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in the computer 110 is generally a collection of data stored on a computer-readable medium, such as a storage medium, a random-access memory, etc.

A computer-readable medium includes any medium that participates in providing data (e.g., instructions), which may be read by a computer 110. Such a medium may take many forms, including, but not limited to, non-volatile media, volatile media, etc. Non-volatile media include, for example, optical or magnetic disks and other persistent memory. Volatile media include dynamic random-access memory (DRAM), which typically constitutes a main memory. Common forms of computer-readable media include, for example, a floppy disk, a flexible disk, hard disk, magnetic tape, any other magnetic medium, a CD ROM, DVD, any other optical medium, punch cards, paper tape, any other physical medium with patterns of holes, a RAM, a PROM, an EPROM, a FLASH EEPROM, any other memory chip or cartridge, or any other medium from which a computer 110 can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. For example, in the process 500, one or more of the steps could be omitted, or the steps could be executed in a different order than shown in FIG. 5. In other words, the descriptions of systems and/or processes herein are provided for the purpose of illustrating certain embodiments and should in no way be construed so as to limit the disclosed subject matter.

Accordingly, it is to be understood that the present disclosure, including the above description and the accompanying figures and below claims, is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

The article "a" modifying a noun should be understood as meaning one or more unless stated otherwise, or context requires otherwise. The phrase "based on" encompasses being partly or entirely based on.

Ordinal adjectives such as "first" and "second" are used throughout this document as identifiers and are not intended to signify importance or order.

The invention claimed is:

1. A system, comprising a computer including a processor and a memory, the memory storing instructions executable by the processor to:
   heat a passenger cabin of a vehicle;
   actuate a thermal sensor to collect temperature data in the passenger cabin;
   identify a surface in the passenger cabin that has a temperature below a temperature threshold; and
   actuate one or more components to sanitize the identified surface.

2. The system of claim 1, wherein the instructions further include instructions to actuate an ultraviolet light toward the identified surface.

3. The system of claim 2, wherein the instructions further include instructions to rotate the ultraviolet light toward the identified surface and to direct ultraviolet rays to the identified surface.

4. The system of claim 2, wherein the instructions further include instructions to actuate the ultraviolet light and a second ultraviolet light to direct ultraviolet rays from both the ultraviolet light and the second ultraviolet light to the identified surface.

5. The system of claim 2, wherein the instructions further include instructions to actuate a second ultraviolet light toward the identified surface when the identified surface is outside an emission range of the ultraviolet light.

6. The system of claim 1, wherein the identified surface is a portion of a window and the instructions further include instructions to actuate a heater to heat the window.

7. The system of claim 6, wherein the heater is an infrared reflective heater disposed in the window.

8. The system of claim 1, wherein the instructions further include instructions to adjust an integrated display in a window to increase insolation into the passenger cabin.

9. The system of claim 1, wherein the instructions further include instructions to collect insolation data from around the vehicle, to identify a direction of highest insolation, and to move the vehicle to align the identified surface along the direction of highest insolation.

10. The system of claim 1, wherein the instructions further include instructions to collect insolation data from around the vehicle, to identify a direction of highest insolation, and to provide a user with instructions to park the vehicle to align the identified surface along the direction of highest insolation.

11. The system of claim 1, wherein the instructions further include instructions to collect insolation data from around the vehicle, to identify an ultraviolet irradiance of the insolation data, and to open one or more windows when the ultraviolet irradiance of insolation data exceeds an irradiance threshold.

12. The system of claim 1, wherein the instructions further include instructions to actuate a motor in a vent to direct air from a heater to the identified surface.

13. The system of claim 1, wherein the instructions further include instructions to actuate a climate control component to heat the passenger cabin.

14. The system of claim 1, wherein the instructions further include instructions to, when an elapsed time that the temperature in the passenger cabin is above the temperature threshold exceeds a time threshold, cease heating the passenger cabin.

15. The system of claim 1, wherein the instructions further include instructions to, upon sanitizing the identified surface, heat the passenger cabin until an elapsed time that the temperature in the passenger cabin is above the temperature threshold exceeds a time threshold.

16. The system of claim 1, wherein the instructions further include instructions to actuate one or more heaters disposed in the passenger cabin to heat the passenger cabin.

17. A method, comprising:
   heating a passenger cabin of a vehicle;
   actuating a thermal sensor to collect temperature data in the passenger cabin;
   identifying a surface in the passenger cabin that has a temperature below a temperature threshold; and actuating one or more components to sanitize the identified surface.

18. The method of claim 17, further comprising actuating an ultraviolet light toward the identified surface.

19. The method of claim 17, wherein the identified surface is a portion of a window and the method further includes actuating a heater to heat the window.

20. The method of claim 17, further comprising actuating a motor in a vent to direct air from a heater to the identified surface.

* * * * *